United States Patent
Hemming et al.

(10) Patent No.: US 9,375,181 B2
(45) Date of Patent: Jun. 28, 2016

(54) FILTERING NOISE FROM A SIGNAL SUBJECTED TO BLANKING

(71) Applicant: Medtronic, Inc., Minneapolis, MN (US)

(72) Inventors: Michael T. Hemming, Kiowa, CO (US); Saul E. Greenhut, Aurora, CO (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/522,938

(22) Filed: Oct. 24, 2014

(65) Prior Publication Data

US 2016/0113586 A1     Apr. 28, 2016

(51) Int. Cl.
  *A61B 5/04*   (2006.01)
  *A61B 5/00*   (2006.01)
  *A61B 5/0402*  (2006.01)

(52) U.S. Cl.
  CPC ............ *A61B 5/7203* (2013.01); *A61B 5/0402* (2013.01); *A61B 5/04012* (2013.01); *A61B 5/686* (2013.01)

(58) Field of Classification Search
  CPC .. A61B 5/686; A61B 5/0402; A61B 5/04012; A61B 5/7203
  See application file for complete search history.

(56) References Cited

U.S. PATENT DOCUMENTS

| | | | |
|---|---|---|---|
| 5,853,364 A * | 12/1998 | Baker et al. ............ | 600/300 |
| 6,915,161 B2 | 7/2005 | Kim | |
| 7,783,354 B2 | 8/2010 | Gunderson | |
| 8,423,135 B2 | 4/2013 | Doerr et al. | |
| 8,744,572 B1 | 6/2014 | Greenhut et al. | |
| 2007/0232945 A1 | 10/2007 | Kleckner et al. | |
| 2007/0232948 A1 | 10/2007 | Stadler et al. | |
| 2011/0196247 A1 | 8/2011 | Cao et al. | |

OTHER PUBLICATIONS (PCT/US2015/055622) PCT Notification of Transmittal of the International Search Report and the Written Opinion of the International Searching Authority, Mailed Jan. 14, 2016, 9 pages.

* cited by examiner

*Primary Examiner* — George Manuel

(57) ABSTRACT

The disclosure describes techniques and systems for filtering noise from a physiological signal. In one example, one or more processors are configured to receive a signal indicative of physiological activity of a patient, wherein the signal comprises noise at one or more frequencies, and filter the noise from the signal according to a noise rejection model, wherein the noise rejection model predicts the noise at the one or more frequencies. The one or more processors may also be configured to, responsive to initiation of a blanking period for the signal, advance the noise rejection model in time during the blanking period, and, responsive to termination of the blanking period, filter, based on the noise rejection model advanced in time, the noise at the one or more frequencies from the signal.

25 Claims, 13 Drawing Sheets

FILTERING NOISE FROM A SIGNAL SUBJECTED TO BLANKING

TECHNICAL FIELD

The disclosure relates to medical devices and, more particularly, medical devices that detect physiological events.

BACKGROUND

Medical devices may monitor physiological activity of a patient. This physiological activity may be tracked to detect one or more physiological events, identify one or more symptoms, diagnose one or more medical conditions, and/or deliver therapy appropriate for the physiological activity. For example, an implantable cardiac device (e.g., a cardiac pacemaker or implantable cardioverter defibrillator (ICD)) may sense electrical activity (e.g., a sensed electrocardiogram (ECG) signal) of a heart of the patient and determine a heart rate of the patient based on the sensed electrical activity. If the cardiac device determines that the heart rate is indicative of an arrhythmia, the cardiac device may deliver pacing pulses or a shock to the heart to correct the arrhythmia.

SUMMARY

In general, the disclosure describes techniques, devices, and systems for filtering noise from a physiological signal. During a blanking period (e.g., a blanking period during which the physiological signal is not received due to a delivered pacing pulse or other delivered or sensed electrical event), the physiological signal is no longer received by a device. Since the noise in the physiological signal cannot be detected during the blanking period, noise artifacts may be created in the filtered signal after the blanking period terminates due to resampling the noise in the physiological signal.

As described herein, a system may generate a noise rejection model for the noise at one or more frequencies in the physiological signal. The system may then filter the noise from the physiological signal according to the noise rejection model. Although the system cannot detect the noise during a blanking period, the system may advance the noise rejection model in time during the blanking period. The system may then, in response to receiving the physiological signal after the blanking period terminates, filter the noise from the physiological signal according to the noise rejection model having been advanced in time. For example, advancing the noise rejection model may predict a phase and/or amplitude of the composite or multi-tone noise (e.g., noise having one or more frequencies) at the termination of the blanking period to reduce or eliminate noise artifacts caused by resampling the noise after the blanking period.

In one example, the disclosure is directed to a method that includes receiving a signal indicative of physiological activity of a patient, wherein the signal comprises noise at one or more frequencies, filtering the noise from the signal according to a noise rejection model, wherein the noise rejection model predicts the noise at the one or more frequencies, responsive to initiation of a blanking period for the signal, advancing the noise rejection model in time during the blanking period, and responsive to termination of the blanking period, filtering, based on the noise rejection model advanced in time, the noise at the one or more frequencies from the signal.

In another example, the disclosure is directed to a device that includes a filtering module configured to receive a signal indicative of physiological activity of a patient, wherein the signal comprises noise at one or more frequencies, filter the noise from the signal according to a noise rejection model, wherein the noise rejection model predicts the noise at the one or more frequencies, responsive to initiation of a blanking period for the signal, advance the noise rejection model in time during the blanking period, and responsive to termination of the blanking period, filter, based on the noise rejection model advanced in time, the noise at the one or more frequencies from the signal.

In another example, the disclosure is directed to a system that includes means for receiving a signal indicative of physiological activity of a patient, wherein the signal comprises noise at one or more frequencies, means for filtering the noise from the signal according to a noise rejection model, wherein the noise rejection model predicts the noise at the one or more frequencies, means for, responsive to initiation of a blanking period for the signal, advancing the noise rejection model in time during the blanking period, and means for, responsive to termination of the blanking period, filtering, based on the noise rejection model advanced in time, the noise at the one or more frequencies from the signal.

In another example, the disclosure is directed to a computer-readable storage medium including instruction that, when executed, cause one or more processors to receive a signal indicative of physiological activity of a patient, wherein the signal comprises noise at one or more frequencies, filter the noise from the signal according to a noise rejection model, wherein the noise rejection model predicts the noise at the one or more frequencies, responsive to initiation of a blanking period for the signal, advance the noise rejection model in time during the blanking period, and responsive to termination of the blanking period, filter, based on the noise rejection model advanced in time, the noise at the one or more frequencies from the signal.

The details of one or more examples are set forth in the accompanying drawings and the description below. Other features, objects, and advantages of the disclosure will be apparent from the description and drawings, and from the claims.

DETAILED DESCRIPTION

Figure 1:
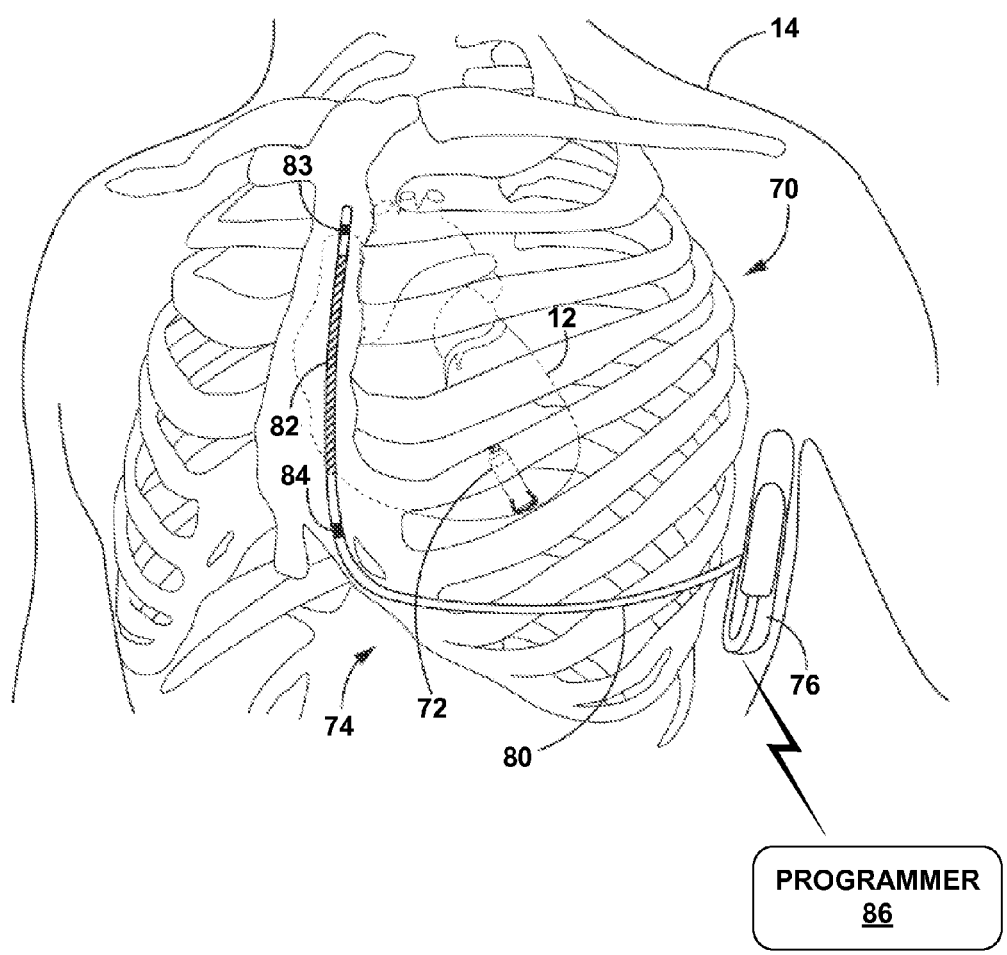
FIG. 1 is a conceptual drawing illustrating an example system that includes a subcutaneous implantable cardioverter defibrillator (subcutaneous ICD) implanted exterior to the rib cage of a patient and a leadless pacing device (LPD) implanted within a cardiac chamber of the patient, in accordance with this disclosure.

This disclosure describes techniques and systems for filtering noise from a physiological signal. A sensed physiological signal may include noise (e.g., components of a signal that do not include desired information) from a variety of sources. Such sensed physiological signals may include electrical signals sensed from a heart, brain, or muscles of a patient. In some examples, at least some of the noise in a signal may be due to electromagnetic interference (EMI), such as EMI line frequencies at 50 Hz, 60 Hz, 100 Hz, and 120 Hz. The EMI noise can prevent a medical device from accurately detecting physiological events (e.g., cardiac rhythms) in a patient and delivering therapy (e.g., pacing, cardioversion, or defibrillation) appropriate to treat the physiological events.

Typically, a medical device may include a noise detector (e.g., an EMI detector) and/or selective notch filters that remove known frequencies of noise from a physiological signal (e.g., a sensed electrocardiogram (ECG)). However, noise artifacts can be generated from these notch filters when the physiological signal is subject to blanking periods (e.g., periods of time during which a sensor is disconnected from an input to avoid sensing an event such as a pacing or defibrillation pulse). In some cases, the medical device temporarily stops receiving the physiological signal for a duration of a blanking period. A pacing signal or cardioversion/defibrillation signal may be delivered to the patient, or some other electrical event may occur, that would otherwise interfere with the physiological signal during the blanking period. Since the noise in the physiological signal cannot be detected during the blanking period and the blanking period is not aligned, or synchronous, with the frequencies of the noise, the phase of the noise at the beginning of the blanking period is typically different than the phase of the noise at the end of the blanking period. The medical device may thus, after the blanking period terminates, generate a filtered signal with noise artifacts due to resampling noise in the physiological signal that has a non-contiguous phase.

As described herein, a system (e.g., an implantable or external medical device) may filter noise (e.g., signal components at target frequencies) from a physiological signal according to a noise rejection model generated for the physiological signal. During blanking periods in which the physiological signal is not available to the system, the system may advance the noise rejection model in time. In other words, the system may step the noise rejection model forward in time (e.g., forward the noise rejection model in real time along with the time of the blanking period) during the blanking period to match an approximate phase and amplitude of the noise when the blanking period terminates. The system may then, in response to receiving the physiological signal after the blanking period terminates, filter the noise from the physiological signal according to the noise rejection model having been advanced in time. Advancing the noise rejection model may thus track a phase and/or amplitude of the noise during the blanking period to reduce or eliminate noise artifacts otherwise caused by resampling the noise after the blanking period.

The system may generate the noise rejection model for the noise at one or more frequencies (e.g., composite or multitone noise) in the physiological signal. For example, the system may detect one or more target frequencies (e.g., EMI frequencies) in the physiological signal and model the detected targeted frequencies. The system may generate the noise rejection model as a finite impulse response (FIR) model using least means square (LMS) adaptation or any other type of adaption or autonomous learning models. The system may generate the noise rejection model in response to detecting the noise. Alternatively, the system may receive a generic noise rejection model as part of an operational instruction set to be used at all times or in response to noise appropriate to the model being detected. The targeted frequencies for the noise rejection model may be preselected based on known frequencies from typical noise sources, e.g., EMI line frequencies, and/or frequencies for which standard notch filters have been used. Alternatively, the system may detect frequencies that are not expected in the type of signals anticipated from the source (e.g., a heart of the patients). In either example, the system may adapt, or update, the noise rejection model over time to address the detected noise, pause adapting the noise rejection model during blanking periods, and/or pause adapting the noise rejection model in response to detecting the absence of noise at the target one or more frequencies.

The system may provide more accurate monitoring of physiological activity of the patient by filtering the noise using the noise rejection model and advancing the noise rejection model during blanking periods. In an example of cardiac cycle detection from ECG signals, the system may reduce oversensing (e.g., detecting more frequent cardiac cycles than are occurring) during normal sinus rhythms or bradycardia by limiting post-blanking period noise artifacts exceeding an R-wave threshold. Conversely, the system may reduce undersensing (e.g., detecting less frequent cardiac cycles than are occurring) during tachyarrhythmias by limiting post-blanking period noise artifacts that cause the system to increase an R-wave threshold above physiological R-wave amplitudes. The system may be configured to deliver therapy (e.g., pacing, cardioversion, or defibrillation signals) to the patient based on the filtered output signal. Alternatively, the system may transmit the filtered output signal to another device configured to deliver a therapy to the patient.

Various types of medical devices, implanted and external, may be configured to filter noise as described herein. For example, subcutaneous devices (e.g., subcutaneous implantable cardioverter defibrillator (subcutaneous ICD) 76 of FIG. 1) and intracardiac devices (e.g., devices with at least one component within the heart such as IMD 16 of FIG. 2 and leadless pacing device (LPD) 16 of FIG. 1) and may employ the noise rejection model described herein. These devices may monitor or diagnose physiological activity, deliver therapy to treat the detected physiological activity, and/or communicate with a device that delivers therapy. In other examples, loop recorders (e.g., ECG or EEG recorders) may also implement the noise filtering techniques described herein.

FIG. 1 is a conceptual drawing illustrating an example cardiac system 70 implanted within a patient 14. Cardiac system 70 includes a subcutaneous ICD system 74 implanted above the ribcage and sternum and a leadless cardiac pacing device (LPD) 72 implanted within a heart 12 of patient 14. External programmer 86 may be configured to communicate with one or both of LPD 72 and subcutaneous ICD 74. As will be described in further detail herein, subcutaneous ICD system 74 and/or LPD 72 may be configured to filter noise from a received physiological signal using a noise rejection model.

Subcutaneous ICD system 74 includes a subcutaneous implantable cardiac defibrillator (subcutaneous ICD) 76 connected to at least one implantable cardiac defibrillation lead 80. Subcutaneous ICD 76 of FIG. 1 is implanted subcutaneously on the left side of patient 14 under the skin but above the ribcage in the example of FIG. 1. Defibrillation lead 80 extends subcutaneously under the skin but above the ribcage from subcutaneous ICD 76 toward a center of the torso of patient 14, bends or turns near the center of the torso, and extends subcutaneously superior under the skin but above the ribcage and/or sternum. Defibrillation lead 80 may be offset laterally to the left or the right of the sternum or located over the sternum. Defibrillation lead 80 may extend substantially parallel to the sternum or be angled lateral from the sternum at either the proximal or distal end.

In other instances, lead 80 may be implanted at other extravascular locations. Lead 80 may be implanted at least partially in a substernal location, e.g., between the ribcage and/or sternum and heart. In one such configuration, a proximal portion of lead 80 extends subcutaneously from subcutaneous ICD 76 toward the sternum (not seen in FIG. 1) and a distal portion of lead 80 extends superior under or below the sternum in the anterior mediastinum. The anterior mediastinum is bounded laterally by the pleurae, posteriorly by the pericardium, and anteriorly by the sternum. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 80 extends along the posterior side of the sternum substantially within the loose connective tissue and/or substernal musculature of the anterior mediastinum. Lead 80 may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum or ribcage.

Defibrillation lead 80 includes an insulative lead body having a proximal end that includes a connector configured to be connected to subcutaneous ICD 76 and a distal portion that includes one or more electrodes. Defibrillation lead 80 also includes one or more conductors that form an electrically conductive path within the lead body and interconnect the electrical connector and respective ones of the electrodes.

Defibrillation lead 80 includes a defibrillation electrode 82 toward the distal portion of defibrillation lead 80, e.g., toward the portion of defibrillation lead 80 extending along the sternum. Defibrillation lead 80 is placed along sternum such that a therapy vector between defibrillation electrode 82 and a housing electrode formed by or on subcutaneous ICD 76 (or other second electrode of the therapy vector) is substantially across a ventricle of heart 12. The therapy vector may, in one example, be viewed as a line that extends from a point on defibrillation electrode 82 (e.g., a center of the defibrillation electrode 82) to a point on the housing electrode of subcutaneous ICD 76. Defibrillation electrode 82 may, in one example, be an elongated coil electrode.

Defibrillation lead 80 may also include one or more sensing electrodes, such as sensing electrodes 83 and 84, located along the distal portion of defibrillation lead 80. In the example illustrated in FIG. 1, sensing electrodes 83 and 84 are separated from one another by defibrillation electrode 82. In other examples, however, sensing electrodes 83 and 84 may be both distal of defibrillation electrode 82 or both proximal of defibrillation electrode 82. In other examples, lead 80 may include more or fewer electrodes.

ICD system 74 may sense electrical signals via one or more sensing vectors that include combinations of electrodes 83 and 84 and the housing electrode of subcutaneous ICD 76. For example, subcutaneous ICD 76 may obtain electrical signals sensed using a sensing vector between electrodes 83 and 84, obtain electrical signals sensed using a sensing vector between electrode 83 and the conductive housing electrode of subcutaneous ICD 76, obtain electrical signals sensed using a sensing vector between electrode 84 and the conductive housing electrode of subcutaneous ICD 76, or a combination thereof. In some instances, subcutaneous ICD 76 may even sense cardiac electrical signals using a sensing vector that includes defibrillation electrode 82 and one of electrodes 83 and 84 or the housing electrode of subcutaneous ICD 76.

The sensed electrical intrinsic signals may include electrical signals generated by cardiac muscle and indicative of depolarizations and repolarizations of heart 12 at various times during the cardiac cycle. Additionally, the sensed electrical signals may also include electrical signals, e.g., pacing pulses, generated and delivered to heart 12 by LPD 72. Subcutaneous ICD 76 analyzes the electrical signals sensed by the one or more sensing vectors to detect tachyarrhythmia, such as ventricular tachycardia or ventricular fibrillation. In response to detecting the tachycardia, subcutaneous ICD 76 may begin to charge a storage element, such as a bank of one or more capacitors, and, when charged, deliver one or more defibrillation shocks via defibrillation electrode 82 of defibrillation lead 80 if the tachyarrhythmia is still present and determined to require defibrillation therapy. Subcutaneous ICD 76 may analyze the sensed electrical signals (e.g., a type of physiological signal) on lead 80 to detect pacing therapy provided by LPD 72 and, in response to detecting the pacing therapy, modifies the sensing and/or tachyarrhythmia detection to reduce the likelihood that the pacing therapy negatively impacts the sensing and detection of subcutaneous ICD 76.

As described above, cardiac system 70 also includes at least one LPD 72. In the example illustrated in FIG. 1, LPD 72 is an implantable leadless pacing device that provides pacing therapy to heart 12 via a pair of electrodes carried on the housing of LPD 72. An example cardiac pacing device is described in U.S. patent application Ser. No. 13/756,085 to Greenhut et al., entitled "SYSTEMS AND METHODS FOR LEADLESS PACING AND SHOCK THERAPY," the entire content of which is incorporated herein by reference. Since LPD 72 includes two or more electrodes carried on the exterior its housing, no other leads or structures need to reside in other chambers of heart 12.

In the example of FIG. 1, LPD 72 is implanted within right ventricle of heart 12 to sense electrical activity of heart 12 and deliver pacing therapy, e.g., anti-tachycardia pacing (ATP) therapy, bradycardia pacing therapy, and/or post-shock pacing therapy, to heart 12. LPD 72 may be attached to a wall of the right ventricle of heart 12 via one or more fixation elements that penetrate the tissue. These fixation elements may secure LPD 72 to the cardiac tissue and retain an electrode (e.g., a cathode or an anode) in contact with the cardiac tissue. However, in other examples, system 70 may include additional LPDs 72 within respective chambers of heart 12 (e.g., right or left atrium and/or left ventricle). In further examples, LPD 72 may be attached to an external surface of heart 12 (e.g., in contact with the epicardium) such that LPD 72 is disposed outside of heart 12.

LPD 72 may be capable sensing electrical signals using the electrodes carried on the housing of LPD 72. These electrical signals may be electrical signals generated by cardiac muscle and indicative of depolarizations and repolarizations of heart 12 at various times during the cardiac cycle. LPD 72 may analyze the sensed electrical signals to detect tachyarrhytmias, such as ventricular tachycardia or ventricular fibrillation. In response to detecting the tachyarrhythmia, LPD 72 may, e.g., depending on the type of tachyarrhythmia, begin to deliver ATP therapy via the electrodes of LPD 72. In addition to or instead of ATP therapy, LPD 72 may also deliver bradycardia pacing therapy and post-shock pacing therapy.

Cardiac pacing device 16 and subcutaneous ICD system 14 are configured to operate completely independent of one another. In other words, LPD 72 and subcutaneous ICD system 74 may not be capable of establishing telemetry communication sessions with one another to exchange information about sensing and/or therapy using one-way or two-way communication. Instead, each of LPD 72 and subcutaneous ICD system 74 analyze the data sensed via their respective electrodes to make tachyarrhythmia detection and/or therapy decisions. As such, each device may not know if the other will detect the tachyarrhythmia, if or when it will provide therapy, and the like.

During a tachyarrhythmia that could be treated with either ATP or a defibrillation shock, it is important to ensure that ATP therapies do not overlap or take place after the defibrillation shock. Applying ATP after a defibrillation shock could be pro-arrhythmic and present a hazard to the patient. Moreover, the delivery of the pacing from LPD 72 could interference with sensing and tachyarrhythmia detection of subcutaneous ICD 76. This interference could take the form of decreased sensitivity (e.g., inability to detect ventricular tachycardia (VT) and/or ventricular fibrillation (VF)) or decreased specificity (e.g., inability to withhold therapy for tachyarrhythmia's determined to not require a defibrillation shock, such as supraventricular tachycardia (SVT), sinus tachycardia (ST), normal sinus rhythm, atrial fibrillation, atrial flutter, or the like). Systems could be designed to provide device-to-device communication between subcutaneous ICD system 74 and LPD 72, but this may add complexity to the system and not be highly effective or fast enough to prevent unwanted ATP therapies post defibrillation shock. The techniques described herein reduce and, in some cases, eliminate the interference with sensing and tachyarrhythmia detection of subcutaneous ICD 76.

Although FIG. 1 is described in the context of a subcutaneous ICD system 74 and a LPD 72, the techniques may be applicable to other coexistent systems. For example, an ICD system that includes a lead having a distal portion that is implanted at least partially under the sternum (or other extrapericardial location) instead of being implanted above the ribs and/or sternum. As another example, instead of a leadless pacing device, a pacing system may be implanted having a pacemaker and one or more leads connected to and extending from the pacemaker into one or more chambers of the heart or attached to the outside of the heart to provide pacing therapy to the one or more chambers (e.g., IMD 16 of FIG. 2). As such, the example of FIG. 1 is illustrated for exemplary purposes only and should not be considered limiting of the techniques described herein.

Figure 2:
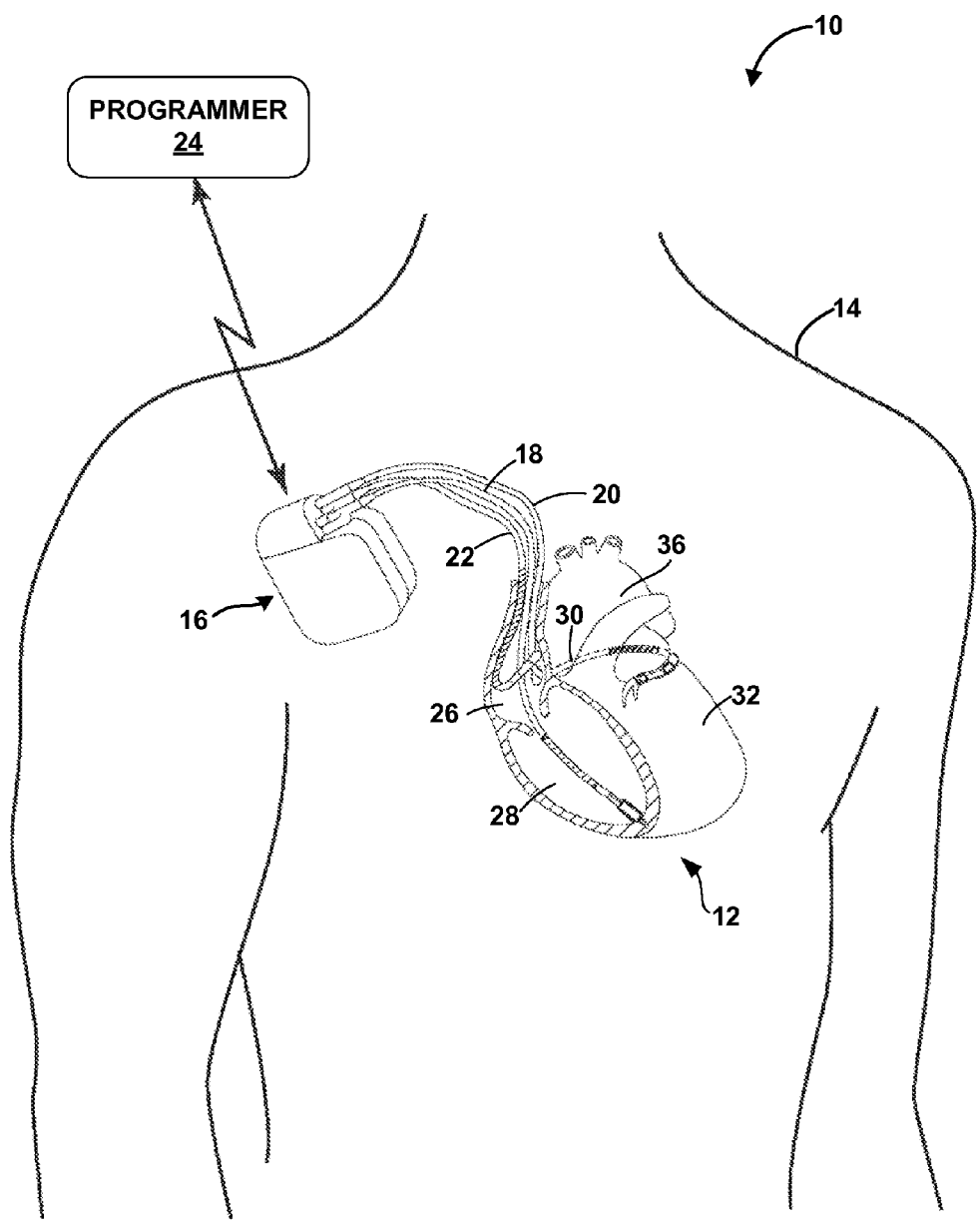
FIG. 2 is a conceptual drawing illustrating an example system that includes an implantable medical device (IMD) coupled to implantable medical leads, in accordance with this disclosure.

External programmer 86 may be similar to programmer 24 of FIG. 2 and may be configured to communicate with one or both of subcutaneous ICD 76 and LPD 72. In this manner, programmer 86 may be configured to give directions to subcutaneous ICD 76 and LPD 72, receive filtered signals, receive sensed events from the filtered signals, or otherwise exchange data. In examples where external programmer 86 only communicates with one of subcutaneous ICD 76 and LPD 72, the non-communicative device may receive instructions from or transmit data to the device in communication with programmer 86. In some examples, programmer 86 comprises a handheld computing device, computer workstation, or networked computing device. Programmer 86 may include a user interface that receives input from a user. In other examples, the user may also interact with programmer 86 remotely via a networked computing device. The user may interact with programmer 86 to communicate with LPD 72 and/or subcutaneous ICD 76. For example, the user may interact with programmer 86 to send an interrogation request and retrieve therapy delivery data, receive filtered physiological signals, update therapy parameters that define therapy, manage communication between LPD 72 and/or subcutaneous ICD 76, or perform any other activities with respect to LPD 72 and/or subcutaneous ICD 76. Although the user is a physician, technician, surgeon, electrophysiologist, or other healthcare professional, the user may be patient 14 in some examples.

Programmer 86 may communication with LPD 72 and/or subcutaneous ICD 76 via wireless communication using any techniques known in the art. Examples of communication techniques may include, for example, radiofrequency (RF) telemetry, but other techniques are also contemplated. In some examples, programmer 86 may include a programming head that may be placed proximate to the patient's body near the LPD 72 and/or subcutaneous ICD 76 implant site in order to improve the quality or security of communication between LPD 72 and/or subcutaneous ICD 76 and programmer 86. In any example, subcutaneous ICD 76 may communicate with one or more leadless or leaded devices implanted internal or external to heart 12.

As discussed herein, system 70 may be configured to sense a physiological signal indicative of a physiological activity of patient 14 and generate a filtered output signal to remove noise over periods of time that include blanking periods. For example, subcutaneous ICD 76 may include one or more processors configured to receiving a signal indicative of physiological activity (e.g., a physiological signal) of patient 14, wherein the physiological signal comprises noise at one or more frequencies (e.g., target frequencies of the noise). Subcutaneous ICD 76 may filter the noise from the signal according to a noise rejection model. The noise rejection model may predict the noise at the one or more frequencies that would occur within the physiological signal.

Subcutaneous ICD 76 may modify the filtering process during blanking periods in which the physiological signal is not received. Subcutaneous ICD 76 may determine the initiation of a blanking period for the physiological signal and, responsive to the initiation of the blanking period, advance the noise rejection model in time during the blanking period. For example, the advancement in time may correspond to the duration of the blanking period. Subcutaneous ICD 76 may then, responsive to termination of the blanking period, filter, based on the noise rejection model advanced in time, the noise at the one or more frequencies from the signal. In this manner, subcutaneous ICD 76 may use the noise rejection model, as it has been advanced in time during the blanking period, to match one or more aspects of the noise in the noise rejection model to the actual noise present in the physiological signal at the termination of the blanking period.

In some examples, the physiological activity indicated by the physiological signal may be electrical activity of heart 12 of patient 14 such as an electrocardiogram (ECG). In other examples, the physiological activity may be a cardiovascular pressure, blood flow, oxygen level, or any other activity. The techniques described herein may alternatively be applied to other physiological signals such as muscle activity, brain activity, or any other activity of patient 14. Although electrical signals sensed from patient 14 may be subjected to noise, other sensors may generate output signals having noise of target frequencies that may be filtered as described herein.

In one example, electromagnetic interference (EMI) may cause at least some of the noise in the physiological signal. EMI line frequencies may have large amplitudes relative to electrical signals sensed from patient 14 and need to be filtered out of sensed signals to uncover the physiological activity of patient 14. Example EMI frequencies of the noise in a physiological signal may include one or more of 50 Hz, 60 Hz, 100 Hz, and 120 Hz. The noise described herein may include a single frequency or the noise may be composite or multi-tone noise having two or more frequencies. However, any frequencies may be target frequencies of noise to be removed from the physiological signal. The noise may include continuous sine wave noise or noise with other wave shapes.

Blanking periods described herein may be a period during which a pacing signal (e.g., a pacing pulse) is delivered to patient 14. However, blanking periods may also, or alternatively, include periods of time during which a defibrillation pulse or other electrical signal is delivered to patient 14 that may interfere with the sensed physiological signal. In other examples, the blanking period may be capture detection blanking that occurs immediately in response to detecting an event to prevent redetecting another event too quickly. As such, subcutaneous ICD 76 may not receive the physiological signal during a blanking period. The physiological signal may be disconnected from sensing circuitry. Alternatively, subcutaneous ICD 76 may be instructed to disregard the physiological signal received during the blanking period.

In some examples, subcutaneous ICD 76 may determine aspects of the blanking period (e.g., the initiation, duration, and/or termination of the blanking period). Subcutaneous ICD 76 may also be configured to initiate and terminate the blanking period. Determination of the aspects of the blanking period, as described herein, includes different ways in which subcutaneous ICD 76, or another device, identifies or sets the blanking period. For example, subcutaneous ICD 76 may determine aspects of the blanking period by setting or establishing the blanking period. Since subcutaneous ICD 76 may also control delivery of a pacing (e.g., via communication with LPD 72, lead or other device) or defibrillation pulse, subcutaneous ICD 76 may set the blanking period to encompass the time during which a pulse is delivered (e.g., the blanking period starts at or before the pulse and ends after the pulse stops). In other words, subcutaneous ICD 76 may set the timing of the blanking period and use that information to advance the noise rejection model during the blanking period. In other examples where subcutaneous ICD 76 incorporates a blanking period for a pacing pulse or defibrillation pulse delivered by another device (e.g., LPD 72), subcutaneous ICD 76 may determine the blanking period by identifying when the pulse is delivered by the other device. Subcutaneous ICD 76 may then set the blanking period (e.g., initiation, duration, and/or termination of the blanking period) based on a communication from the other device indicating when the pulse will be delivered or in response to detecting that the pulse was delivered. The duration of the blanking period may be predetermined time and/or variable based on the duration or other aspect of the delivered pulse. Subcutaneous ICD 76 may thus determine aspects of the blanking period and advance the noise rejection model during this blanking period. A processor, filtering module, sensing module, or other component of subcutaneous ICD 76 may be configured to initiate and/or terminate each blanking period.

In some examples, subcutaneous ICD 76 may generate a noise rejection model by first detecting the noise at one or more frequencies in the received physiological signal. Subcutaneous ICD 76 may include instructions indicating the one or more target frequencies to be filtered or removed from the physiological signal, and subcutaneous ICD 76 may detect which one of those target frequencies are present in the signal. Alternatively, subcutaneous ICD 76 may process the physiological signal for any frequencies not typically associated with the intended physiological activity and identify those frequencies as noise to be removed. Subcutaneous ICD 76 may detect parameters of the noise other than the frequency, such as amplitude, wave shape, and phase. Subcutaneous ICD 76 may monitor the noise for a predetermined time or for a predetermined number of cycles of the detected noise frequency in order to generate the noise rejection model. Subcutaneous ICD 76 may then model the detected noise to include those detected parameters of the signal. In this manner, subcutaneous ICD 76 may generate the noise rejection model for the noise from the received physiological signal.

Subcutaneous ICD 76 may generate the noise rejection model and continue to use the noise rejection model over time to filter the noise from the physiological signal. In some examples, subcutaneous ICD 76 may continue to adapt, based on the received signal, the noise rejection model as the physiological signal is received. In other words, subcutaneous ICD 76 may continually update the noise rejection model based on the received physiological signal. Subcutaneous ICD 76 may thus continue to detect the noise in the signal over time and update the noise rejection model as needed to facilitate removal of non-stationary noise signal sources. Subcutaneous ICD 76 may pause or otherwise stop adapting the noise rejection model in some situations. For example, subcutaneous ICD 76 may pause the adaption of the noise rejection model during the blanking period. Since subcutaneous ICD 76 does not receive the physiological signal, and thus the noise within the signal, during the blanking period, subcutaneous ICD 76 would not be capable of updating the noise rejection model during the blanking period. Subcutaneous ICD 76 may pause the adaptation or updating of the noise rejection model in response to detecting that the noise is not present in the received physiological signal. In other examples, subcutaneous ICD 76 may periodically update the noise rejection model based on a predetermined schedule or update the noise rejection model in response to receiving an indication that the filtered output signal includes anomalies indicative of improper sensing (e.g., oversensing or undersensing) or receiving a user request to update the noise rejection model.

In some examples, subcutaneous ICD 76 may generate the noise rejection model as a finite impulse response (FIR) model. In other examples, subcutaneous ICD 76 may generate the noise rejection model as a non-linear summing multi-layer model (e.g., a neural model) or an auto-regressive model (e.g., an infinite impulse response model). Each of these or other types models may be used to model, or estimate, the noise in the physiological signal. subcutaneous ICD 76 may develop the FIR model (or other types of models) using least means square (LMS) adaptation or some other adaptive learning algorithms (e.g., gradient algorithms, a root mean square (RMS) adaptive estimation or a recursive lease squares (RLS)). In this manner, subcutaneous ICD 76 may update or adapt the noise rejection model using different techniques, some of which may be selected based on the source or type of noise. Subcutaneous ICD 76 may update the noise rejection model continually, periodically, or in response to an indication that the noise rejection model is not removing the noise (e.g., detection of oversensing, undersensing, or other filtered output anomalies).

Subcutaneous ICD 76, or any other device, may initially generate the noise rejection model in response to detecting the noise. In other words, subcutaneous ICD 76 may not have a noise rejection model stored in memory until the noise is detected and the noise rejection model is generated to remove the detected noise. Alternatively, subcutaneous ICD 76 may receive a generic noise rejection model as part of an operational instruction set. The generic noise rejection model may be directed to a particular type of noise signal, type of frequency or frequencies, or other aspects of the noise. However, subcutaneous ICD 76 may adapt or update the generic noise rejection model to remove the specific frequencies, amplitudes, waveshapes, or other aspects of the noise as described herein.

During the blanking period, subcutaneous ICD 76 may continue to monitor the expected noise. Since the physiological signal is not available during the blanking period, subcutaneous ICD 76 may use the noise rejection model to track the expected noise over the duration of the blanking period. In this manner, the noise rejection model may allow subcutaneous ICD 76 to accurately predict attributes of the noise in the physiological signal as soon as the physiological signal is again received after the blanking period terminates. For example, subcutaneous ICD 76 may advance the noise rejection model by calculating, for each of the one or more target frequencies of the noise, a phase change of the noise rejection model for a duration of the blanking period. This phase change may be the extent to which the phase of one or more noise signals has changed during the blanking period. For each of the one or more target frequencies, subcutaneous ICD 76 may then determine, based on the calculated phase change in the noise rejection model, an expected phase and an expected amplitude of the noise in the received signal to predictive of an actual phase and an actual amplitude of the noise in the received signal at the termination of the blanking period. In other words, subcutaneous ICD 76 may time step the noise rejection model in real-time during the blanking period to immediately filter the noise from the physiological signal received immediately upon termination of the blanking period. In some examples, subcutaneous ICD 76 may calculate a parameter other than phase of the noise during the blanking period to track any particular type of signal represented by the noise rejection model.

In some examples, subcutaneous ICD 76 may process the received physiological signal to detect whether or not the noise is present in the signal. Responsive to determining that no noise is present in the physiological signal at the target frequencies, subcutaneous ICD 76 may stop applying the noise rejection model to filter the physiological signal. Subcutaneous ICD 76 may detect that noise is present at a target frequency when a signal magnitude at the target frequency exceeds a pre-determined threshold magnitude, for example. In other examples, subcutaneous ICD 76 may terminate filtering of the noise in response to determining the initiation of the blanking period since the physiological signal is not received during the blanking period.

As described herein, subcutaneous ICD 76 may receive a physiological signal from patient 14. In addition, subcutaneous ICD 76 may be configured to deliver therapy to patient 14 to treat physiological events or activities in response to detecting an event from the filtered physiological signal. For example, subcutaneous ICD 76 may be configured to deliver cardioversion and/or defibrillation shocks to heart 12. Subcutaneous ICD 76 may deliver one or more therapies in response to detecting an event in the filtered physiological signal described herein. Prior to, and for the duration of, delivering a therapeutic pulse or signal to heart 12, subcutaneous ICD 76 may initiate a blanking period for the physiological signal. Subcutaneous ICD 76 may accurately monitor physiological activity of patient 14 over period of time that includes blanking periods by filtering the physiological signal with a noise rejection model advanced in time during the blanking periods.

FIG. 2 is a conceptual drawing illustrating an example system 10 that includes an implantable medical device (IMD) 16 for delivering therapy to heart 12 and filtering noise using a noise rejection model. Therapy system 10 may perform functions similar to system 70 of FIG. 1. In other words, IMD 16, subcutaneous ICD 76, and/or LPD 72 may filter a physiological signal with a noise rejection model as described herein. Therapy system 10 includes IMD 16, which is coupled to leads 18, 20, and 22, and external programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily, a human patient. In other examples, IMD 16 may monitor a physiological signal from patient 14 without delivering therapy. IMD 16 may be referred to as a device, apparatus, or system in some examples.

Although an implantable medical device and delivery of electrical stimulation to heart 12 are described herein as examples, the techniques for filtering a physiological signal over time periods that include one or more blanking periods may be applied using other medical devices and with or without other therapies. In general, the techniques described in this disclosure may be implemented by any medical device, e.g., implantable or external, that includes or is coupled to two or more electrodes or any other sensor configured to detect a physiological activity of patient 14. As one alternative example, IMD 16 may be a neurostimulator that delivers electrical stimulation to and/or monitor conditions associated with the brain, spinal cord, or neural tissue of patient 16. As a second alternative example, IMD 16 may be a diagnostic device coupled to two subcutaneous electrodes at different positions in the thorax of patient 14 that monitors a cardiac signal of patient 14, and does not deliver therapy to the patient.

In the example of FIG. 2, leads 18, 20, 22 extend into the heart 12 of patient 16 to sense electrical activity of heart 12 and/or deliver electrical stimulation to heart 12. In the example shown in FIG. 2, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, therapy system 10 may additionally or alternatively include one or more leads or lead segments (not shown in FIG. 2) that deploy one or more electrodes within the vena cava or other vein. These electrodes may allow alternative electrical sensing configurations that may provide improved or supplemental sensing in some patients. Furthermore, in some examples, therapy system 10 may additionally or alternatively include temporary or permanent epicardial or subcutaneous leads, instead of or in addition to transvenous, intracardiac leads 18, 20 and 22. Such leads may be used for one or more of cardiac sensing, pacing, and/or cardioversion/defibrillation.

IMD 16 may sense electrical signals attendant to the depolarization and repolarization of heart 12 via electrodes (not shown in FIG. 1) coupled to at least one of the leads 18, 20, and 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32 (and/or a right or left atrium), and may also provide defibrillation therapy and/or cardioversion therapy via electrodes located on at least one of the leads 18, 20, and 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In some examples, programmer 24 comprises a handheld computing device, computer workstation, or networked computing device. Programmer 24 may include a user interface that receives input from a user. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16, such as filtered output signals from a sensed physiological signal, generated noise rejection models, or other related data. A user may also interact with programmer 24 (e.g., similar to programmer 86 of FIG. 1) to program IMD 16, e.g., select values for operational therapy parameters of the IMD (such as target frequencies of noise) and configure autonomic diagnostic functions.

For example, the user may use programmer 24 to retrieve information from IMD 16 regarding the rhythm of heart 12, trends therein over time, or arrhythmic episodes. In some examples, programmer 24 may retrieve raw sensed physiological signals and/or filtered output signals as described herein. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16. In some examples, this information may be presented to the user as an alert. For example, a lead related condition identified based on noise sensed subsequent to delivery of an electrical signal may trigger IMD 16 to transmit an alert to the user via programmer 24. In addition, a sensed decrease in thoracic impedance variability may trigger an alert to programmer 24 that there may be an increase in heart failure probability.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 3:
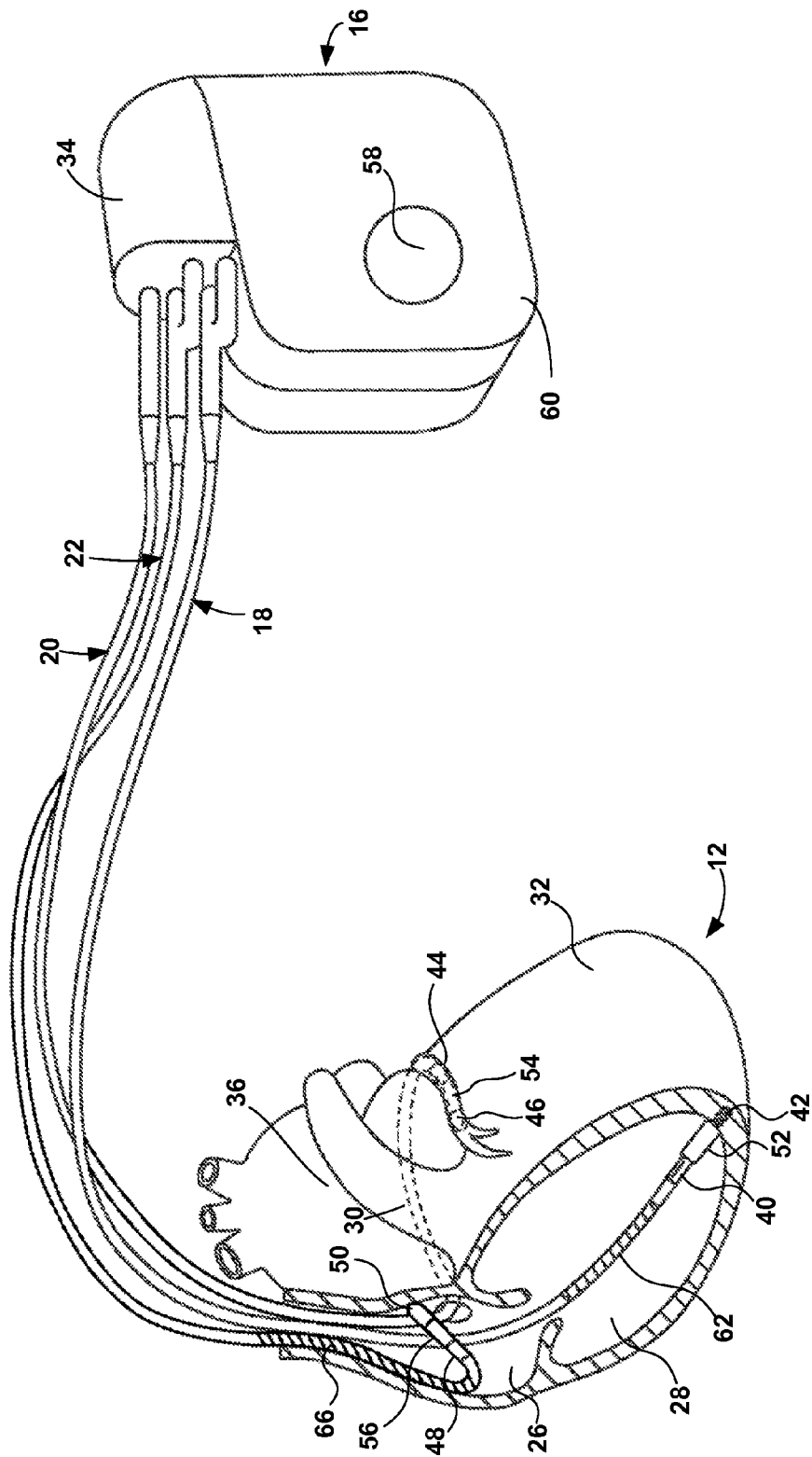
FIG. 3 is a conceptual drawing illustrating the example IMD and leads of FIG. 2 in conjunction with a heart.

FIG. 3 is a conceptual drawing illustrating IMD 16 and leads 18, 20, and 22 of system 10 in greater detail. Leads 18, 20, and 22 may be electrically coupled to a signal generator, e.g., stimulation generator, and a sensing module of IMD 16 via connector block 34. In some examples, proximal ends of leads 18, 20, and 22 may include electrical contacts that electrically couple to respective electrical contacts within connector block 34 of IMD 16. In addition, in some examples, leads 18, 20, and 22 may be mechanically coupled to connector block 34 with the aid of set screws, connection pins, snap connectors, or another suitable mechanical coupling mechanism.

Each of the leads 18, 20, and 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other examples, one or more of electrodes 42, 46, and 50 may take the form of small circular electrodes at the tip of a tined lead or other fixation element. Leads 18 and 22 also include elongated electrodes 62 and 66, respectively, which may take the form of a coil. Each of the electrodes 40, 42, 44, 46, 48, 50, 62, and 66 may be electrically coupled to a respective one of the coiled conductors within the lead body of its associated lead 18, 20, and 22, and thereby coupled to respective ones of the electrical contacts on the proximal end of leads 18, 20, and 22.

In some examples, as illustrated in FIG. 3, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 5, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, and 66. The electrical signals are conducted to IMD 16 from the electrodes via the respective leads 18, 20, and 22. IMD 16 may sense such electrical signals via any bipolar combination of electrodes 40, 42, 44, 46, 48, 50, 62, and 66. Furthermore, any of the electrodes 40, 42, 44, 46, 48, 50, 62, and 66 may be used for unipolar sensing in combination with housing electrode 58. The combination of electrodes used for sensing may be referred to as a sensing configuration. IMD 16 may use one or more sensing configurations to receive a physiological signal indicative of physiological activity of heart 12. This physiological signal may be susceptible to noise from external sources, for example.

In some examples, IMD 16 delivers pacing pulses via bipolar combinations of electrodes 40, 42, 44, 46, 48, and 50 to produce depolarization of cardiac tissue of heart 12. In other examples, IMD 16 delivers pacing pulses via any of electrodes 40, 42, 44, 46, 48, and 50 in combination with housing electrode 58 in a unipolar configuration. Furthermore, IMD 16 may deliver defibrillation pulses to heart 12 via any combination of elongated electrodes 62, 66, and housing electrode 58. Electrodes 58, 62, and 66 may also be used to deliver cardioversion pulses to heart 12. Electrodes 62 and 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of therapy system 10 illustrated in FIGS. 2 and 3 is merely one example. In other examples, a therapy system may include epicardial leads and/or patch electrodes instead of or in addition to the transvenous leads 18, 20, and 22 illustrated in FIG. 2. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 2 and 3, and an additional lead located within or proximate to left atrium 36. As another example, other therapy systems may include a single lead that extends from IMD 16 into right atrium 26 or right ventricle 28, or two leads that extend into a respective one of the right ventricle 26 and right atrium 26. Any electrodes located on these additional leads may be used in sensing and/or stimulation configurations.

Additionally, as previously mentioned, IMD 16 need not deliver therapy to heart 12. In general, this disclosure may be applicable to any medical device, e.g., implantable or external, that includes electrodes to sense physiological signals, deliver electrical stimulation to patient 14, and/or measure intrathoracic impedance.

In other examples, a therapy system may be similar to therapy system 10 of FIGS. 2 and 3, but includes two leads 18 and 22, rather than three leads. Leads 18 and 22 may be implanted within right ventricle 28 and right atrium 26, respectively. A two lead system may be useful for providing defibrillation and pacing pulses to heart 12. In any case, physiological signals received from any electrodes of a therapy system and/or monitoring system may use a noise rejection model to reduce noise artifacts typically cause by blanking periods.

Figure 4:
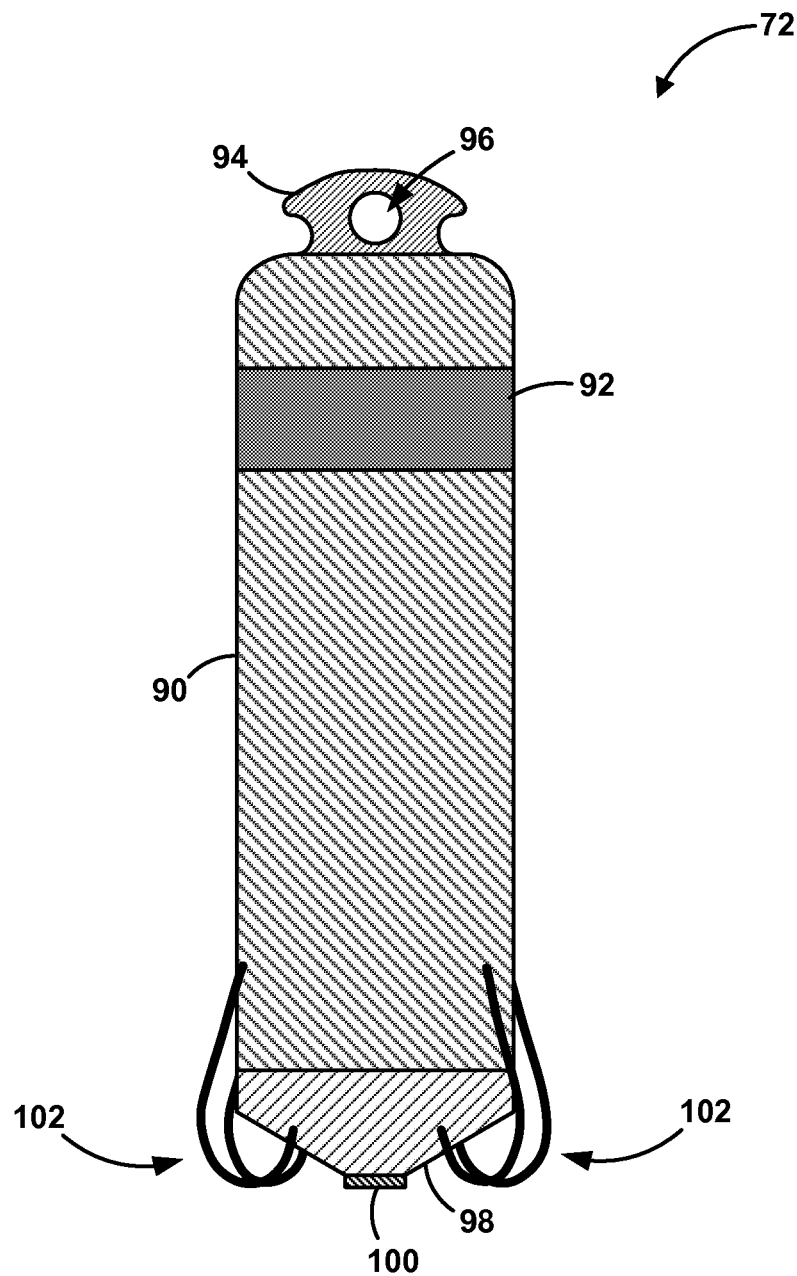
FIG. 4 is a conceptual drawing illustrating the example LPD of FIG. 1.

FIG. 4 is a conceptual drawing illustrating the example LPD 72 of FIG. 1. As shown in FIG. 4, LPD 72 includes case 90, cap 98, electrode 100, electrode 92, fixation mechanisms 102, flange 94, and opening 96. Together, case 90 and cap 98 may be considered the housing of LPD 72. In this manner, case 90 and cap 98 may enclose and protect the various electrical components within LPD 72. Case 90 may enclose substantially all of the electrical components, and cap 98 may seal case 90 and create the hermetically sealed housing of LPD 72. Although LPD 72 is generally described as including one or more electrodes, LPD 72 may typically include at least two electrodes (e.g., electrodes 92 and 100) to deliver an electrical signal (e.g., therapy such as ATP) and/or provide at least one sensing vector.

Electrodes 92 and 100 are carried on the housing created by case 90 and cap 98. In this manner, electrodes 92 and 100 may be considered leadless electrodes. In the example of FIG. 4, electrode 100 is disposed on the exterior surface of cap 98. Electrode 100 may be a circular electrode positioned to contact cardiac tissue upon implantation. Electrode 92 may be a ring or cylindrical electrode disposed on the exterior surface of case 90. Both case 90 and cap 98 may be electrically insulated. Electrode 100 may be used as a cathode and electrode 92 may be used as an anode, or vice versa, for delivering pacing stimulation therapy such as ATP or post-shock pacing. However, electrodes 92 and 100 may be used in any stimulation configuration. In addition, electrodes 92 and 100 may be used to detect intrinsic electrical signals from cardiac muscle. In other examples, LPD 72 may include three or more electrodes, where each electrode may deliver therapy and/or detect intrinsic signals.

Fixation mechanisms 102 may attach LPD 72 to cardiac tissue. Fixation mechanisms 62 may be active fixation tines, screws, clamps, adhesive members, or any other types of attaching a device to tissue. As shown in the example of FIG. 4, fixation mechanisms 102 may be constructed of a memory material that retains a preformed shape. During implantation, fixation mechanisms 102 may be flexed forward to pierce tissue and allowed to flex back towards case 90. In this manner, fixation mechanisms 92 may be embedded within the target tissue.

Flange 94 may be provided on one end of case 90 to enable tethering or extraction of LPD 72. For example, a suture or other device may be inserted around flange 94 and/or through opening 96 and attached to tissue. In this manner, flange 94 may provide a secondary attachment structure to tether or retain LPD 72 within heart 12 if fixation mechanisms 102 fail. Flange 94 and/or opening 96 may also be used to extract LPD 72 once the LPD needs to be explanted (or removed) from patient 14 if such action is deemed necessary.

Figure 5:
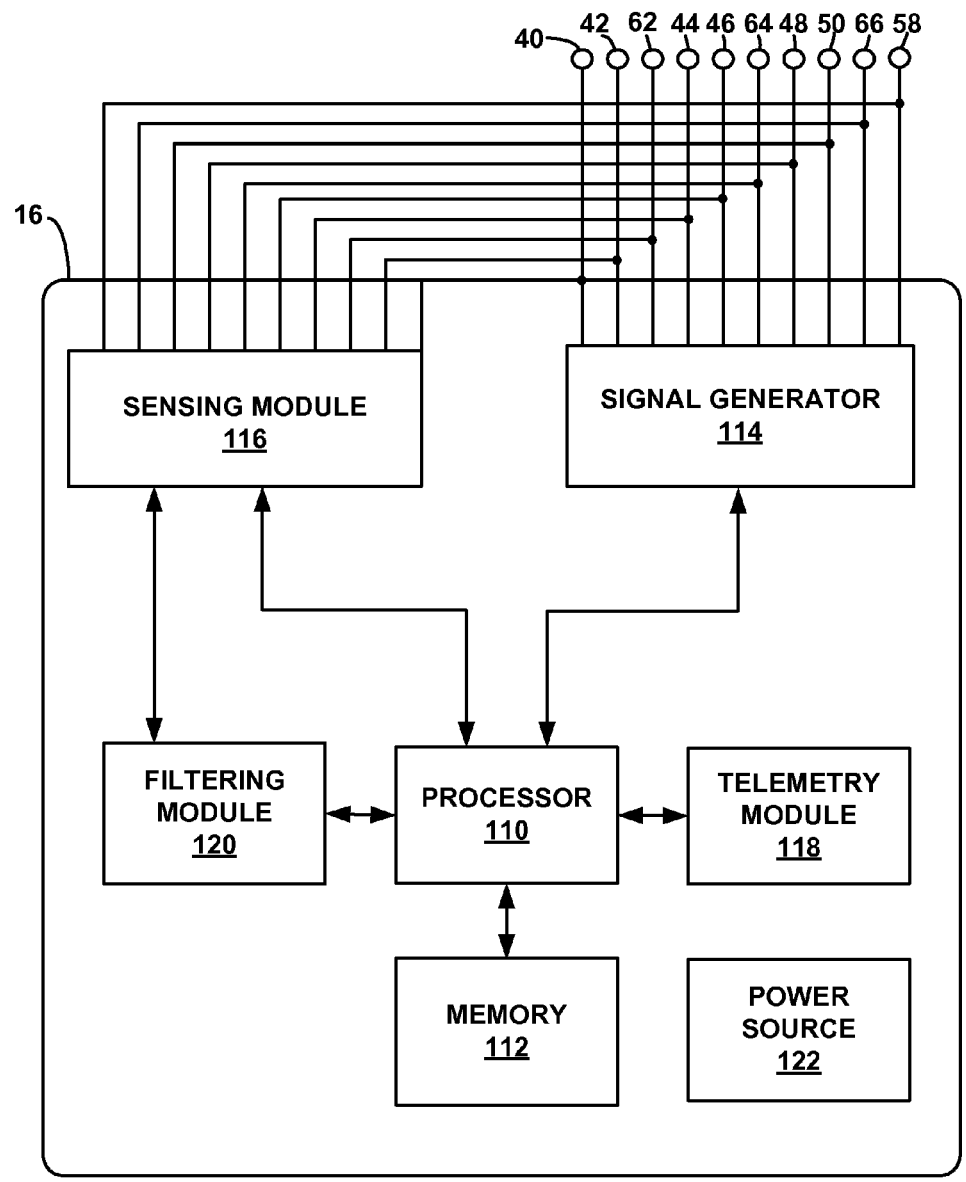
FIG. 5 is a functional block diagram illustrating an example configuration of the IMD of FIG. 2.

FIG. 5 is a functional block diagram illustrating an example configuration of IMD 16 of FIG. 2. In the illustrated example, IMD 16 includes a processor 110, memory 112, signal generator 114, sensing module 116, telemetry module 118, filtering module 120, and power source 122. Memory 112 includes computer-readable instructions that, when executed by processor 110, cause IMD 16 and processor 110 to perform various functions attributed to IMD 16 and processor 110 herein. Memory 112 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. In other examples, IMD 16 may include fewer or greater components than shown in FIG. 5.

Processor 110 may include any one or more of a microprocessor, a controller, a digital signal processor (DSP), an application specific integrated circuit (ASIC), a field-programmable gate array (FPGA), or equivalent discrete or analog logic circuitry. In some examples, processor 110 may include multiple components, such as any combination of one or more microprocessors, one or more controllers, one or more DSPs, one or more ASICs, or one or more FPGAs, as well as other discrete or integrated logic circuitry. The functions attributed to processor 110 herein may be embodied as software, firmware, hardware or any combination thereof.

Processor 110 may control signal generator 114 to deliver stimulation therapy to heart 12 according to a selected one or more of therapy programs, which may be stored in memory 112. For example, processor 110 may control stimulation generator 84 to deliver electrical pulses with the amplitudes, pulse widths, frequency, or electrode polarities specified by the selected one or more therapy programs. In some examples, processor 110 may control signal generator 114 to deliver stimulation therapy in response to one or more physiological events identified from the filtered physiological signal output by filtering module 120.

Signal generator 114 is electrically coupled to electrodes 40, 42, 44, 46, 48, 50, 58, 62 and 66, e.g., via conductors of the respective lead 18, 20, and 22, or, in the case of housing electrode 58, via an electrical conductor disposed within housing 60 of IMD 16. In the illustrated example, signal generator 114 is configured to generate and deliver electrical stimulation therapy to heart 12. For example, signal generator 114 may deliver defibrillation shocks to heart 12 via at least two electrodes 58, 62, and 66. Signal generator 114 may deliver pacing pulses via ring electrodes 40, 44, and 48 coupled to leads 18, 20, and 22, respectively, and/or helical electrodes 42, 46, and 50 of leads 18, 20, and 22, respectively. In some examples, signal generator 114 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 114 may include a switch module and processor 110 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 116 monitors signals from at least one of electrodes 40, 42, 44, 46, 48, 50, 58, 62, or 66 in order to monitor electrical activity of heart 12. These signals may be physiological signals. Sensing module 116 may also include a switch module to select which of the available electrodes are used to sense the heart activity, depending upon which electrode combination is used in the current sensing configuration. In some examples, processor 110 may select the electrodes that function as sense electrodes, i.e., select the sensing configuration, via the switch module within sensing module 116. Processor 110 may control the functionality of sensing module 116 by providing signals via a data/address bus.

Sensing module 116 may include one or more detection channels, each of which may comprise an amplifier. The detection channels may be used to sense the cardiac signals. Some detection channels may detect events, such as R- or P-waves, and provide indications of the occurrences of such events to processor 110. One or more other detection channels may provide the signals to an analog-to-digital converter, for processing or analysis by processor 110. In response to the signals from processor 110, the switch module within sensing module 116 may couple selected electrodes to selected detection channels.

For example, sensing module 116 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 110 then uses that detection in measuring frequencies of the sensed events. Different narrow band channels of sensing module 116 may have distinct functions. For example, some various narrow band channels may be used to sense either atrial or ventricular events.

In one example, at least one narrow band channel may include an R-wave amplifier that receives signals from the sensing configuration of electrodes 40 and 42, which are used for sensing and/or pacing in right ventricle 28 of heart 12. Another narrow band channel may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Furthermore, in some examples, one or more of the sensing channels of sensing module 116 may be selectively coupled to housing electrode 58, or elongated electrodes 62 or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 116 includes a wide band channel which may comprise an amplifier with a relatively wider pass band than the R-wave or P-wave amplifiers. Signals from the selected sensing electrodes that are selected for coupling to this wide-band amplifier may be converted to multi-bit digital signals by an analog-to-digital converter (ADC) provided by, for example, sensing module 116 or processor 110. In some examples, processor 110 may store the digitized versions of signals from the wide band channel in memory 112 as electrograms (EGMs).

In some examples, processor 110 may employ digital signal analysis techniques to characterize the digitized signals from the wide band channel to, for example detect and classify the patient's heart rhythm. Processor 110 may detect and classify the patient's heart rhythm by employing any of the numerous signal processing methodologies known in the art.

Processor 110 may maintain one or more programmable interval counters. If IMD 16 is configured to generate and deliver pacing pulses to heart 12, processor 110 may maintain programmable counters which control the basic time intervals associated with various modes of pacing, including cardiac resynchronization therapy (CRT) and anti-tachycardia pacing (ATP). In examples in which IMD 16 is configured to deliver pacing therapy, intervals defined by processor 110 may include atrial and ventricular pacing escape intervals, refractory periods during which sensed P-waves and R-waves are ineffective to restart timing of the escape intervals, and the pulse widths of the pacing pulses. As another example, processor 110 may define a blanking period, and provide signals to sensing module 116 to blank one or more channels, e.g., amplifiers, for a period during and after delivery of electrical stimulation to heart 12. The durations of these intervals may be determined by processor 110 in response to stored data in memory 112. Processor 110 may also determine the amplitude of the cardiac pacing pulses.

Processor 110 may reset interval counters upon sensing of R-waves and P-waves with detection channels of sensing module 116. For pacing, signal generator 114 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 110 may also reset the interval counters upon the generation of pacing pulses by signal generator 114, and thereby control the basic timing of cardiac pacing functions, including CRT and ATP.

The value of the count present in the interval counters when reset by sensed R-waves and P-waves may be used by processor 110 to measure the durations of R-R intervals, P-P intervals, PR intervals and R-P intervals, which are measurements that may be stored in memory 112. Processor 110 may use the count in the interval counters to detect a tachyarrhythmia event, such as ventricular fibrillation or ventricular tachycardia. In some examples, a portion of memory 112 may be configured as a plurality of recirculating buffers, capable of holding series of measured intervals, which may be analyzed by processor 110 to determine whether the patient's heart 12 is presently exhibiting atrial or ventricular tachyarrhythmia.

In some examples, processor 110 may determine that tachyarrhythmia has occurred by identification of shortened R-R (or P-P) interval lengths. Generally, processor 110 detects tachycardia when the interval length falls below 220 milliseconds (ms) and fibrillation when the interval length falls below 180 ms. These interval lengths are merely examples, and a user may define the interval lengths as desired, which may then be stored within memory 112. This interval length may need to be detected for a certain number of consecutive cycles, for a certain percentage of cycles within a running window, or a running average for a certain number of cardiac cycles, as examples.

Filtering module 120 may be configured to filter the received physiological signal for any one or more detection channels or electrode configurations and send the filtered output signal to the interval counters, processor 110, or any other structure that detects one or more type of events within the filtered output signal indicative of physiological activity. As described herein, filtering module 120 may generate (or retrieve from device memory) one or more noise rejection models for target frequencies of noise within a received physiological signal (e.g., electrical signal sensed via sensing module 116) and filter the physiological signal according to the noise rejection model. During a blanking period in which sensing module 116 is disconnected from input signals of one or more electrodes 40, 42, 44, 46, 48, 50, 58, 62, and 66 or the physiological signal is otherwise unavailable to filtering module 120, filtering module 120 may advance the noise rejection model in time to account for the duration of time of the blanking period. Upon termination of the blanking period and the physiological signal is again available, filtering module 120 may restart filtering the noise from the physiological signal according to the noise rejection model advanced in time. In this manner, filtering module 120 may reduce or eliminate noise artifacts in the filtered output signal due to resampling the noise at an unknown phase and amplitude upon termination of the blanking period. Filtering module 120 may transmit the filtered output signal back to sensing module 134 in some examples to allow sensing module 116 to identify events within the filtered output signal.

In some examples, filtering module 120 may include a processor, circuitry, firmware, and/or software necessary to perform the noise modeling and filtering techniques described herein. In other examples, processor 110 may control filtering module 120 to perform the filtering of received physiological signals. As shown in FIG. 5, filtering module 120 may be directly coupled to sensing module 116 to receive the physiological signal from sensing module 116 and output the filtered output signal to processor 110. Processor 110 may also be configured to control filtering module 120. In other examples, sensing module 116 may include filtering module 120 or otherwise perform the functions of filtering module 120. In some examples, filtering module 120 may receive the physiological signal from processor 110 or processor 110 may perform the filtering functions of filtering module 120. Alternatively, filtering module 120 may be a software module executed by processor 110 or another processor within IMD 16.

Filtering module 120 and/or processor 110 may then store filtered output signals, generated noise rejection models, or any other information representative of the condition of or the treatment of the patient. Memory 112 may thus store the generated physiological information (e.g., filtered and/or unfiltered physiological signals) along with other operational instructions or memory 112 may include a separate memory for storing the physiological information. If memory 112 has reached capacity, memory 112 may replace the oldest stored physiological information with the new physiological information to prevent the discarding of the newest information.

Telemetry module 118 includes any suitable hardware, firmware, software or any combination thereof for communicating with another device, such as programmer 24 of FIG. 1. Under the control of processor 110, telemetry module 118 may receive downlink telemetry from and send uplink telemetry to programmer 24 with the aid of an antenna, which may be internal and/or external. Processor 110 may provide the data to be uplinked to programmer 24 and the control signals for the telemetry circuit within telemetry module 118, e.g., via an address/data bus. In some examples, telemetry module 118 may provide received data to processor 110 via a multiplexer.

In some examples, processor 110 may transmit atrial and ventricular heart signals (e.g., physiological signals such as electrocardiogram signals) produced by atrial and ventricular sense amp circuits within sensing module 116 and/or filtering module 120 to programmer 24. Programmer 24 may interrogate IMD 16 to receive the physiological signals. Processor 110 may store physiological signals within memory 112, and retrieve stored physiological signals from memory 112. Processor 110 may also generate and store marker codes indicative of different cardiac events that sensing module 116 and/or filtering module 120 detects, and transmit the marker codes to programmer 24.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician.

Figure 6A:
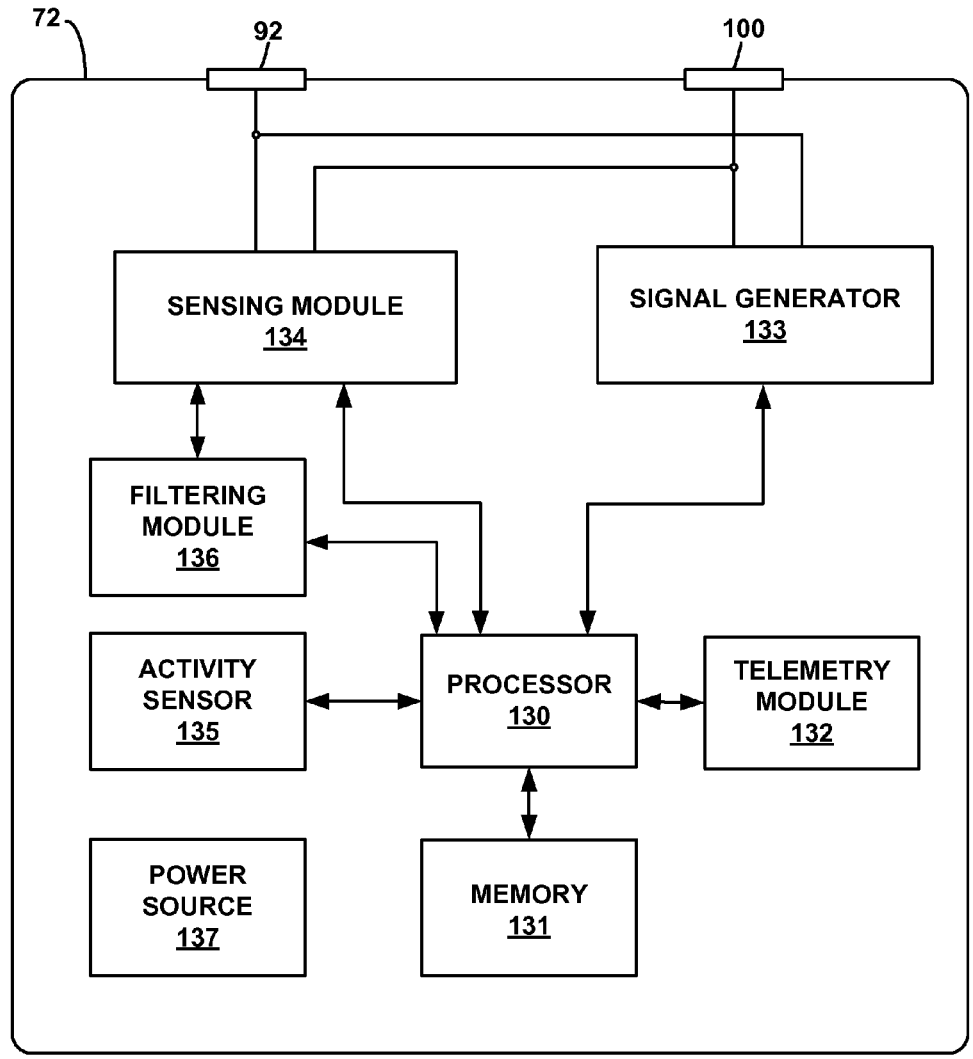
FIG. 6A is a functional block diagram illustrating an example configuration of the LPD of FIG. 1.

FIG. 6A is a functional block diagram illustrating an example configuration of the LPD 72 of FIG. 1. In the illustrated example, LPD 72 includes a processor 130, memory 131, signal generator 133, sensing module 134, filtering module 136, activity sensor 135, telemetry module 132, and power source 137. The components of LPD 72 may be similar to the components of IMD 16 of FIG. 5. For example, processor 130, memory 131, signal generator 133, sensing module 134, filtering module 136, and telemetry module 132 of LPD 72 may be similar to processor 110, memory 112, signal generator 114, sensing module 116, filtering module 120, and telemetry module 118 of IMD 16, respectively. Although LPD 72 is described as being configured to receive a physiological signal and deliver pacing pulses, LPD 72 may not be configured to receive a physiological signal or deliver pacing pulses in other examples. In this manner, LPD 72 may include fewer or greater components than shown in FIG. 6A.

Memory 131 may include computer-readable instructions that, when executed by processor 130, cause LPD 72 and processor 130 to perform various functions attributed to LPD 72 and processor 130 herein (e.g., detecting arrhythmias, communicating with subcutaneous ICD 76, and delivering anti-tachycardia pacing and post-shock pacing). Memory 131 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 130 may include any one or more of a microprocessor, a controller, a digital signal processor (DSP), an application specific integrated circuit (ASIC), a field-programmable gate array (FPGA), or equivalent discrete or analog logic circuitry. In some examples, processor 130 may include multiple components, such as any combination of one or more microprocessors, one or more controllers, one or more DSPs, one or more ASICs, or one or more FPGAs, as well as other discrete or integrated logic circuitry. The functions attributed to processor 130 herein may be embodied as software, firmware, hardware or any combination thereof.

Processor 130 controls signal generator 133 to deliver stimulation therapy to heart 12 according to a therapy parameters, which may be stored in memory 131. For example, processor 130 may control signal generator 133 to deliver electrical pulses with the amplitudes, pulse widths, frequency, or electrode polarities specified by the therapy parameters. In this manner, signal generator 133 may deliver pacing pulses (e.g., pacing pulses, anti-tachycardia pacing (ATP) pulses or post-shock pacing pulses) to heart 12 via electrodes 52 and 60. Although LPD 72 may only include two electrodes, e.g., electrodes 52 and 60, LPD 72 may utilize three or more electrodes in other examples. LPD 72 may use any combination of electrodes to deliver therapy and/or detect electrical signals from patient 14.

Signal generator 133 is electrically coupled to electrodes 52 and 60 carried on the housing of LPD 72. In the illustrated example, signal generator 133 is configured to generate and deliver electrical stimulation therapy to heart 12. For example, signal generator 133 may deliver ATP pulses to a portion of cardiac muscle within heart 12 via electrodes 52 and 60. In some examples, signal generator 133 may deliver pacing stimulation in the form of electrical pulses. In other examples, signal generator may deliver one or more of these types of stimulation in the form of other signals, such as sine waves, square waves, or other substantially continuous time signals. Although LPD 72 is generally described has delivering pacing pulses, LPD 72 may deliver cardioversion or defibrillation pulses in other examples.

Electrical sensing module 134 monitors physiological signals (e.g., electrical signals) from at least one of electrodes 52 and 60 in order to monitor electrical activity of heart 12, impedance, or other electrical phenomenon. Sensing may be done to determine heart rates or heart rate variability, or to detect arrhythmias (e.g., tachyarrhythmias) or other electrical signals. Sensing module 134 may also include a switch module to select which of the available electrodes (or electrode polarity) are used to sense the heart activity, depending upon which electrode combination, or electrode vector, is used in the current sensing configuration. In examples with several electrodes, processor 130 may select the electrodes that function as sense electrodes, i.e., select the sensing configuration, via the switch module within sensing module 134. Sensing module 134 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 130, e.g. Processor 130 may control the functionality of sensing module 134 by providing signals via a data/address bus.

As described herein, filtering module 136 may be configured to generate noise rejection models, advance the noise rejection models in time during blanking periods, and filter a physiological signal after the termination of a blanking period according to the noise rejection model advanced in time. In some examples, filtering module 136 may be in communication with sensing module 134 to receive a physiological signal and transmit the filtered output signal back to sensing module 134 and/or processor 130 for physiological event detection. In other examples, sensing module 134 may include filtering module 136 or processor 130 may perform the filtering functions performed by filtering module 136. The output signal from filtering module 136 may be utilized by sensing module 134 and/or processor 130 to determine any events or characterize the physiological activity of heart 12.

Processor 130 may include a timing and control module, which may be embodied as hardware, firmware, software, or any combination thereof. The timing and control module may comprise a dedicated hardware circuit, such as an ASIC, separate from other processor 130 components, such as a microprocessor, or a software module executed by a component of processor 130, which may be a microprocessor or ASIC. The timing and control module may implement programmable counters. If LPD 72 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 130 may include atrial and ventricular pacing escape intervals, refractory periods during which sensed P-waves and R-waves are ineffective to restart timing of the escape intervals, and the pulse widths of the pacing pulses. Processor 130 may process filtered signals from filtering module 136 to detect such intervals. As another example, the timing and control module may withhold sensing from one or more channels of sensing module 134 for a time interval during and after delivery of electrical stimulation to heart 12. The durations of these intervals may be determined by processor 130 in response to stored data in memory 131. The timing and control module of processor 130 may also determine the amplitude of the cardiac pacing pulses.

Interval counters implemented by the timing and control module of processor 130 may be reset upon sensing of R-waves and P-waves with detection channels of sensing module 134. In examples in which LPD 72 provides pacing, signal generator 133 may include pacer output circuits that are coupled to electrodes 34 and 46, for example, appropriate for delivery of a bipolar or unipolar pacing pulse to one of the chambers of heart 12. In such examples, processor 130 may reset the interval counters upon the generation of pacing pulses by signal generator 133, and thereby control the basic timing of cardiac pacing functions, including ATP or post-shock pacing.

In addition to detecting and identifying specific types of cardiac rhythms (types of cardiac events), sensing module 134 may also sample the detected intrinsic signals to generate an electrogram or other time-based indication of cardiac events (e.g., types of physiological signals). Processor 130 may also be able to coordinate the delivery of pacing pulses from different LPDs implanted in different chambers of heart 12, such as an LPD implanted in atrium 22 and/or an LPD implanted in left ventricle 24. For example, processor 130 may identify delivered pulses from other LPDs via sensing module 134 and updating pulse timing to accomplish a selected pacing regimen. Processor 130 may initiate blanking periods for each of these delivered pacing pulses. This detection may be on a pulse-to-pulse or beat-to-beat basis or on a less frequent basis to make slight modifications to pulse rate over time. In other examples, LPDs may communicate with each other via telemetry module 132 and/or instructions over a carrier wave (such as a stimulation waveform). In this manner, ATP or post-shock pacing may be coordinated from multiple LPDs.

Memory 131 may be configured to store a variety of operational parameters, therapy parameters, sensed and detected data (e.g., unfiltered and/or filtered physiological signals), generated noise rejection models, and any other information related to the therapy and treatment of patient 14. In the example of FIG. 6A, memory 131 may store sensed ECGs, detected arrhythmias, communications from subcutaneous ICD 76, and therapy parameters that define ATP and/or post-shock pacing regimens. In other examples, memory 131 may act as a temporary buffer for storing data until it can be uploaded to subcutaneous ICD 76, another implanted device, or programmer 86.

Activity sensor 135 may be contained within the housing of LPD 72 and include one or more accelerometers or other devices capable of detecting motion and/or position of LPD 72. For example, activity sensor 135 may include a 3-axis accelerometer that is configured to detect accelerations in any direction in space. Specifically, the 3-axis accelerator may be used to detect LPD 72 motion that may be indicative of cardiac events and/or noise. For example, processor 16 may monitor the accelerations from activity sensor 135 to confirm or detect arrhythmias. Since LPD 72 may move with a chamber wall of heart 12, the detected changes in acceleration may also be indicative of contractions. Therefore, LPD 72 may be configured to identify heart rates and confirm arrhythmias, such as a tachycardia, sensed via sensing module 134. In some examples, filtering module 136 may apply the noise rejection models and blanking period filtering to acceleration signals such that blanking periods may prevent multiple events in response to detecting a first physiological event.

Telemetry module 132 includes any suitable hardware, firmware, software or any combination thereof for communicating with another device, such as programmer 86 or subcutaneous ICD 76 (FIG. 1). Under the control of processor 130, telemetry module 132 may receive downlink telemetry from and send uplink telemetry to programmer 86 with the aid of an antenna, which may be internal and/or external. Processor 130 may provide the data to be uplinked to programmer 86 and the control signals for the telemetry circuit within telemetry module 132, e.g., via an address/data bus. In some examples, telemetry module 132 may provide received data to processor 130 via a multiplexer.

In some examples, LPD 72 may signal programmer 86 to further communicate with and pass the alert through a network such as the Medtronic CareLink® Network developed by Medtronic, Inc., of Minneapolis, Minn., or some other network linking patient 14 to a clinician. LPD 72 may spontaneously transmit information to the network or in response to an interrogation request from a user.

In other examples, processor 130 may be configured to transmit information to another device, such as subcutaneous ICD 76 using electrodes 52 and 60. For example, processor 130 may control signal generator 133 to generate electrical signals representative of commands such as the detection of an arrhythmia, confirmation that a tachycardia has been detected, a request to monitor electrical signals for arrhythmias, or even signals to "wake up" an subcutaneous ICD in a sleep mode. In other examples, processor 130 may cause telemetry module 132 to transmit information representative of sensed physiological data such as R-R intervals or any other data that may be used by subcutaneous ICD 76 to determine a condition of patient 14 (e.g., whether or not patient 14 is experiencing an arrhythmia). The communication may be in the form of dedicated communication signals. Alternatively, processor 130 may communicate with subcutaneous ICD 76 by delivering pacing pulses at specific intervals that would be identifiable by subcutaneous ICD 76 as non-physiologic and intended to convey information.

Power source 137 may be any type of device that is configured to hold a charge to operate the circuitry of LPD 72. Power source 137 may be provided as a rechargeable or non-rechargeable battery. In another example, power source 137 may incorporate an energy scavenging system that stores electrical energy from movement of LPD 72 within patient 14.

There may be numerous variations to the configuration of LPD 72, as described herein. In one example, LPD 72 includes a housing configured to be implanted within heart 12 of patient 14, one or more electrodes (e.g., electrodes 52 and 60) coupled to the housing, fixation mechanism 62 configured to attach the housing to tissue of heart 12, sensing module 134 configured to sense an electrical signal from heart 12 of patient 14 via the one or more electrodes, and signal generator 133 configured to deliver ATP therapy to heart 12 of patient 14 via the one or more electrodes. LPD 72 may also include processor 130 configured to receive a communication message from subcutaneous ICD 76 requesting LPD 72 deliver ATP to heart 12, where subcutaneous ICD 76 is configured to be implanted exterior to a rib cage of patient 14. Processor 130 may also be configured to determine, based on the sensed electrical signal, whether to deliver ATP to heart 12, and, in response to the determination, command signal generator 133 to deliver the ATP therapy. Processor 130 may also be configured to control signal generator 133 to deliver post-shock pacing to patient 14 in response to filtering module 136 detecting an anti-tachyarrhythmia shock.

Figure 6B:
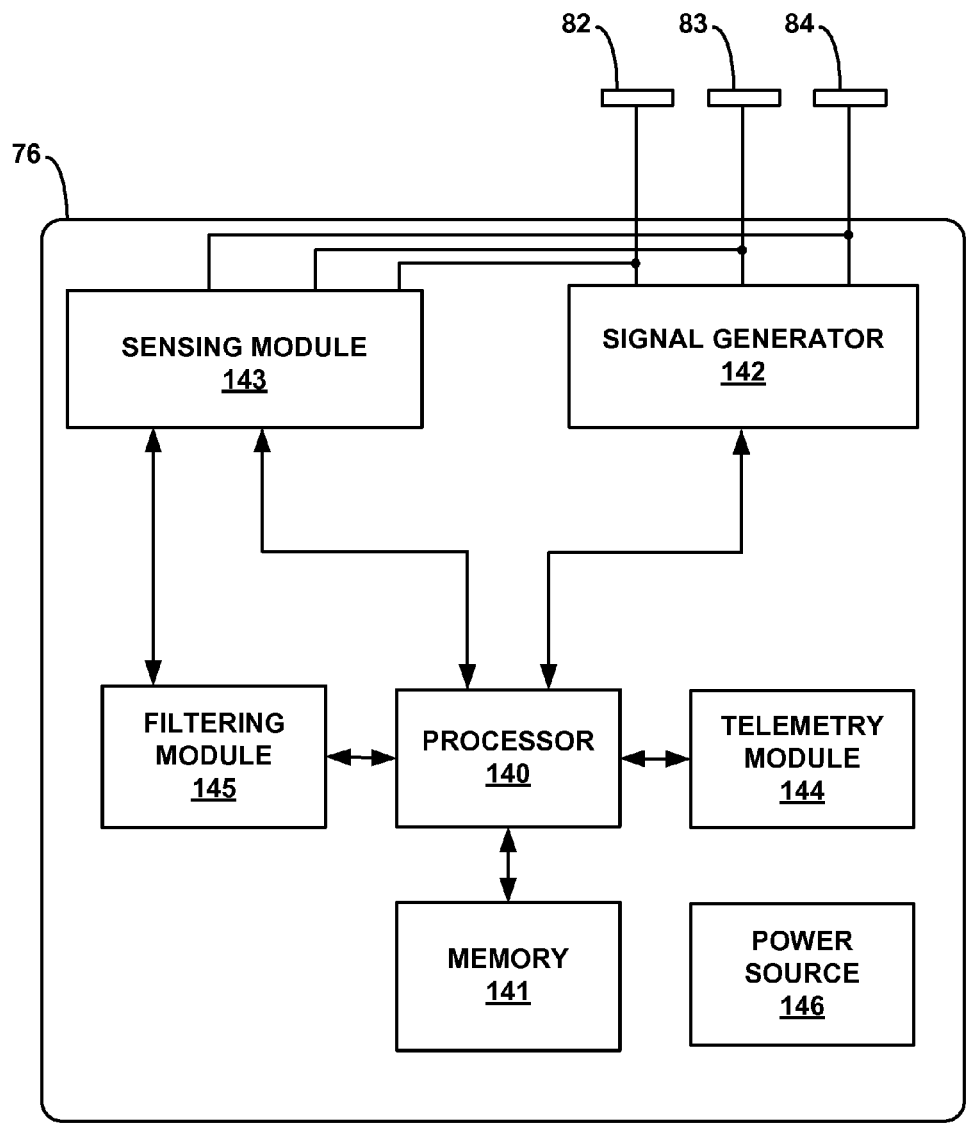
FIG. 6B is a functional block diagram illustrating an example configuration of the subcutaneous ICD of FIG. 1.

FIG. 6B is a functional block diagram illustrating an example configuration of the subcutaneous ICD 76 of FIG. 1. In the illustrated example, subcutaneous ICD 76 includes a processor 140, memory 141, signal generator 142, sensing module 143, filtering module 145, telemetry module 144, and power source 146. The components of subcutaneous ICD 76 may be similar to the components of IMD 16 of FIG. 5 and/or LPD 72 of FIG. 6B. For example, processor 140, memory 141, signal generator 142, sensing module 143, filtering module 145, and telemetry module 144 of subcutaneous ICD 76 may be similar to processor 110, memory 112, signal generator 114, sensing module 116, filtering module 120, and telemetry module 118 of IMD 16, respectively. Although subcutaneous ICD 76 is described as being configured to receive a physiological signal and deliver cardioversion or defibrillation therapy, subcutaneous ICD 76 may perform additional functions or not perform some functions. In this manner, subcutaneous ICD 76 may include fewer or greater components than shown in FIG. 6B.

Figure 7:
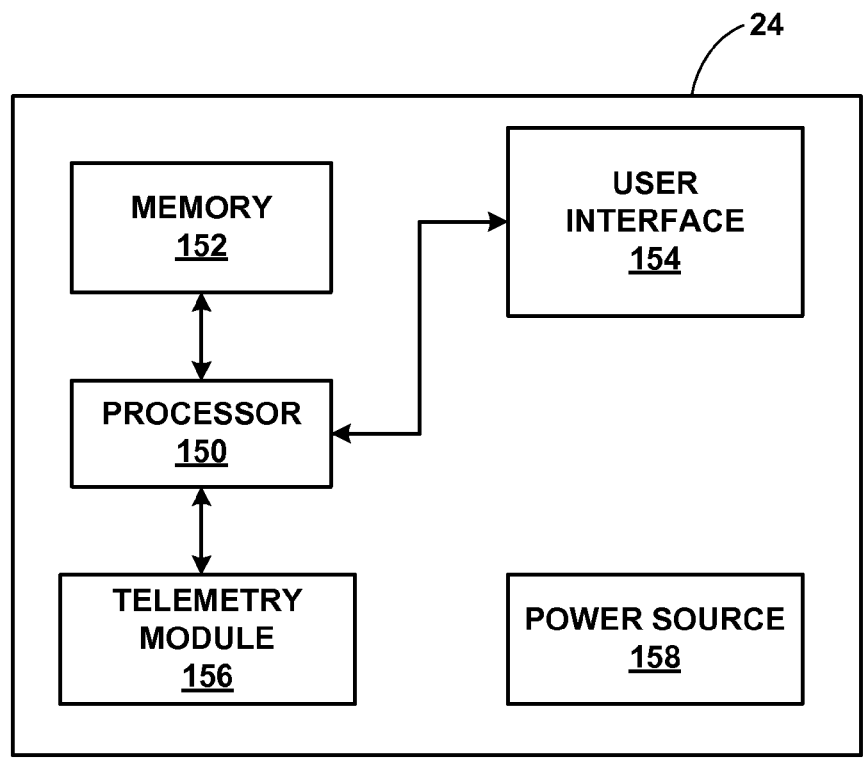
FIG. 7 is a functional block diagram illustrating an example configuration of an external programmer that facilitates user communication with an IMD.

FIG. 7 is a functional block diagram illustrating an example configuration of external programmer 24 that facilitates user communication with IMD 16. Although the description of FIG. 7 is directed to programmer 24 of FIG. 2, programmer 86 of FIG. 1 may include similar components and functions. As shown in FIG. 7, programmer 24 may include a processor 150, memory 152, user interface 154, telemetry module 156, and power source 158. Programmer 24 may be a dedicated hardware device with dedicated software for programming of IMD 16. Alternatively, programmer 24 may be an off-the-shelf computing device (e.g., a mobile computing device such as a smartphone or tablet, a notebook computer, or a workstation) running an application that enables programmer 24 to program IMD 16. In some other examples, programmer 24 may include a filtering module similar to filtering modules 120 of FIG. 5, 136 of FIG. 6A, and filtering modules 145 of FIG. 6B to filter a physiological signal using a noise rejection model advanced in time during blanking periods.

A user may use programmer 24 to select values of operational parameters. The clinician may interact with programmer 24 via user interface 154, which may include display to present graphical user interface to a user, and a keypad or another mechanism for receiving input from a user. The user may also use programmer 24 to adjust or control the target frequencies for the noise to be filtered out of physiological signals, instructions regarding the generation of noise rejection models, types of adaptive filters used to generate the noise rejection models, or any other parameter related to filtering physiological signals subjected to, or not subjected to, blanking periods.

Processor 150 can take the form one or more microprocessors, DSPs, ASICs, FPGAs, programmable logic circuitry, or the like, and the functions attributed to processor 150 herein may be embodied as hardware, firmware, software or any combination thereof. Memory 152 may store instructions that cause processor 150 to provide the functionality ascribed to programmer 24 herein, and information used by processor 150 to provide the functionality ascribed to programmer 24 herein. Memory 152 may include any fixed or removable magnetic, optical, or electrical media, such as RAM, ROM, CD-ROM, hard or floppy magnetic disks, EEPROM, or the like. Memory 152 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 156, which may be coupled to an internal antenna or an external antenna. An external antenna that is coupled to programmer 24 may correspond to the programming head that may be placed over heart 12, as described above with reference to FIG. 1. Telemetry module 156 may be similar to telemetry module 118 of IMD 16 (FIG. 5).

Telemetry module 156 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 150 of programmer 24 and/or one or more processors of one or more networked computers may perform all or a portion of the techniques described herein with respect to IMD 16, LPD 72, subcutaneous ICD 76, or any other medical device. For example, processor 150 or another processor may receive physiological signals and filter noise from the physiological signals with a noise rejection model as described herein.

Figure 8:
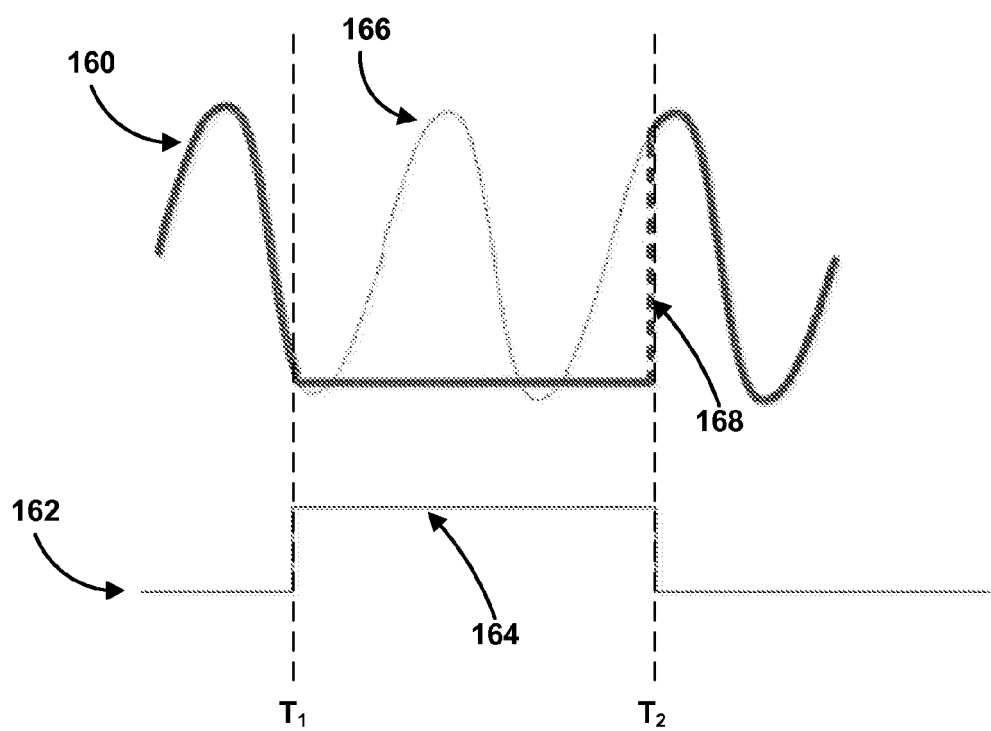
FIG. 8 is a timing diagram of noise in an example signal with respect to a blanking period.

FIG. 8 is a timing diagram of noise 160 in an example signal with respect to a blanking period 164. As shown in FIG. 8, waveform 160 (solid line) may represent noise at a target frequency within a physiological signal. Waveform 162 represents a blanking period during which the physiological signal, and the noise waveform 160, is no longer received. Before blanking period 164, waveform 160 may be received as noise of the target frequency. At time $T_1$, blanking period 164 starts and waveform 160 drops to zero amplitude because the noise is no longer received with the blanked physiological signal. When blanking period 164 terminates at time $T_2$, noise waveform 160 is again received with the physiological signal. Spike 168 is a dotted line that indicates the jump in noise waveform 160 upon the termination of blanking period 165. Spike 168 is the result of blanking period 164 being asynchronous to the phase of noise waveform 160, and spike 168 may cause noise artifacts from this unexpected amplitude of waveform 160 at the end of blanking period 164.

The filtering process described herein may reduce noise artifacts resulting from spike 168 in noise waveform 160. Filtering module 120 of IMD 16, for example, may generate a noise rejection model 166 of noise waveform 160 and filter the noise from waveform 160 out of the physiological signal according to the noise rejection model 166. During blanking period 164, filtering module 120 may advance noise rejection model 166 in time to reflect what waveform 160 should occur during blanking period 164. In other words, filtering module 120 may continue tracking the noise during blanking period 164 so that there is no unexpected spike 168 in the noise upon the termination of blanking period 164. Noise rejection model 166 may thus match the phase and amplitude of noise waveform 160. Since filtering module 120 does not have to resample waveform 160 upon receiving waveform 160 after termination of blanking period 164, filtering module 120 may not introduce noise artifacts into the filtered output signal after each blanking period.

Figure 9:
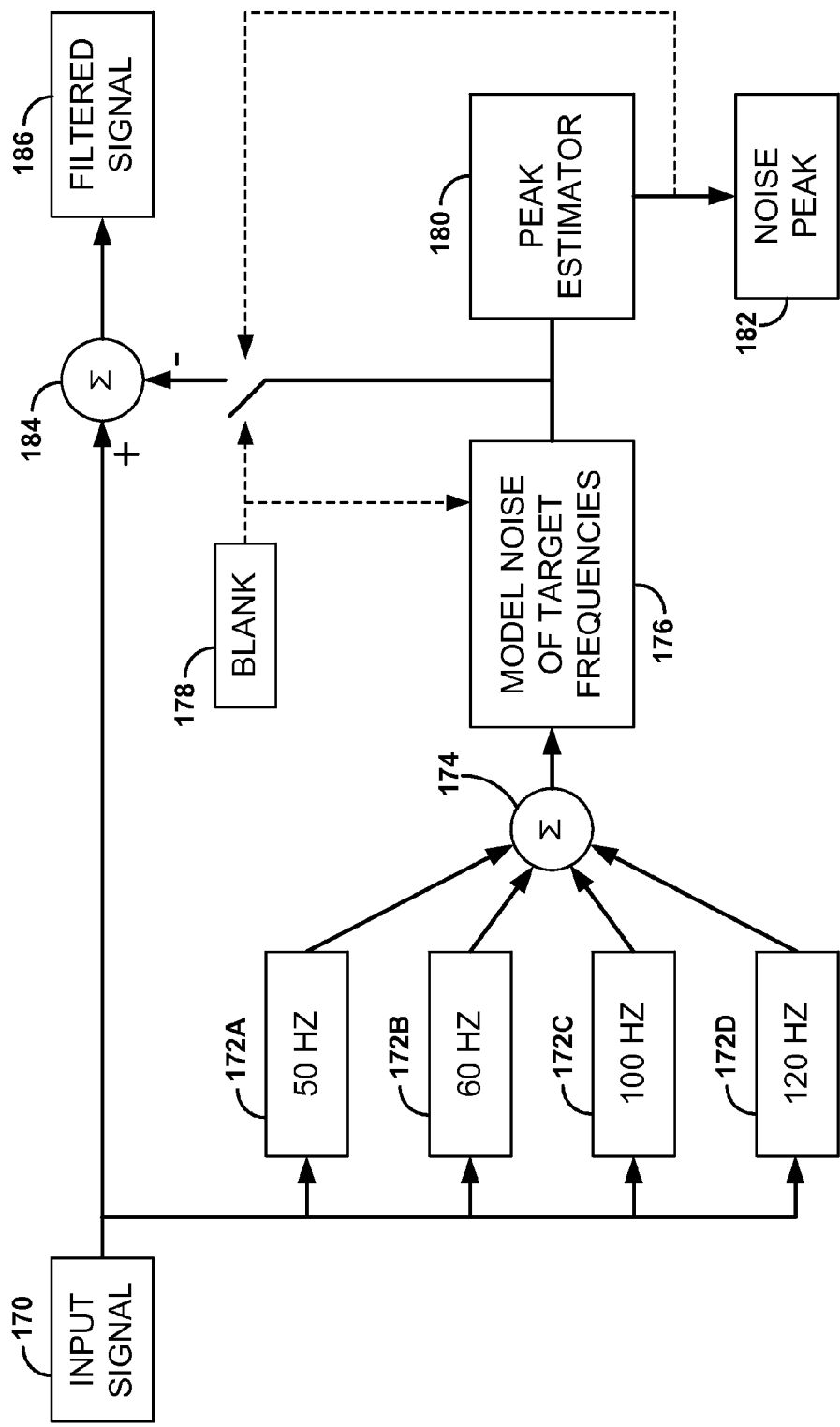
FIG. 9 is a conceptual diagram illustrating an example process for generating a noise rejection model and filtering noise after blanking periods with the noise rejection model.

FIG. 9 is a conceptual diagram illustrating an example process for generating a noise rejection model and filtering noise after blanking periods with the noise rejection model. FIG. 9 will be described with respect to filtering module 120 of IMD 16, but the process of FIG. 9 may also be applied by filtering module 136 of LPD 72, filtering module 145 of subcutaneous ICD 76, or any other processor or module filtering a physiological signal. As shown in FIG. 9, input signal 170 is received and target frequencies 172A, 172B, 172C, and 172D (collectively "target frequencies 172" for the noise are detected and extracted from input signal 170. In the example of FIG. 9, target frequencies 172 include 50 Hz, 60 Hz, 100 Hz, and 120 Hz associated with EMI line frequencies.

Filtering module 120 may then sum target frequencies 172 via a summing operator 174 and generate a noise rejection model 176 of the noise for the target frequencies 172. As described herein, noise rejection model 176 may model noise of a single frequency or composite or multi-tone noise having two or more frequencies. For example, the noise rejection model may be a FIR model that is developed, or adapted, using LMS adaptation. For example, the FIR model may be adapted according to the equation $W_n = W_{n-1} + \mu * \text{ERR}$. Filtering module 120 may stop updating the FIR model during a blanking period (e.g., $\mu = 0$). Filtering module 120 may also stop filtering the physiological signal during the blanking period while continuing to advance the time base of the noise rejection model 176. Blanking indicator 178 opening the gate depicted in FIG. 9 during a blanking period to stop filtering input signal 170 illustrates filtering module 142 ceasing or suspending filtering input signal 170 in response to determination of a blanking period.

Filtering module 120 may also use noise rejection model 176 for peak estimator 180. Peak estimator 180 may identify the peaks within the noise rejection model 176 and output the noise peak 182. Filtering module 120 may use noise peak 182 for diagnostic purposes and/or to open or close the gate controlling the filtering of input signal 170. For example, filtering module 120 may open the gate and stop filtering of input signal 170 if the noise peak 182 does not exceed a threshold. For example, the threshold may be an expected magnitude of the intended electrical signal from the heart. If noise peak 182 is below the threshold, filtering module 120 determines that the noise of the target frequencies 172 is minimal or zero (e.g., EMI line frequencies are not present) and input signal 170 does not need to be filtered or otherwise corrected for the target frequencies.

During filtering, summing operator 184 subtracts the noise rejection model 176 (e.g., the modeled noise) from the input signal 170, and filtering module 120 may output filtered output signal 186. In this manner, filtering module 120 may use noise rejection model 176 to predict the noise that will be in input signal 170 at the end of a blanking period to accurately filter the noise from input signal 170 immediately upon termination of the blanking period and with minimal or zero noise artifacts.

Figure 10:
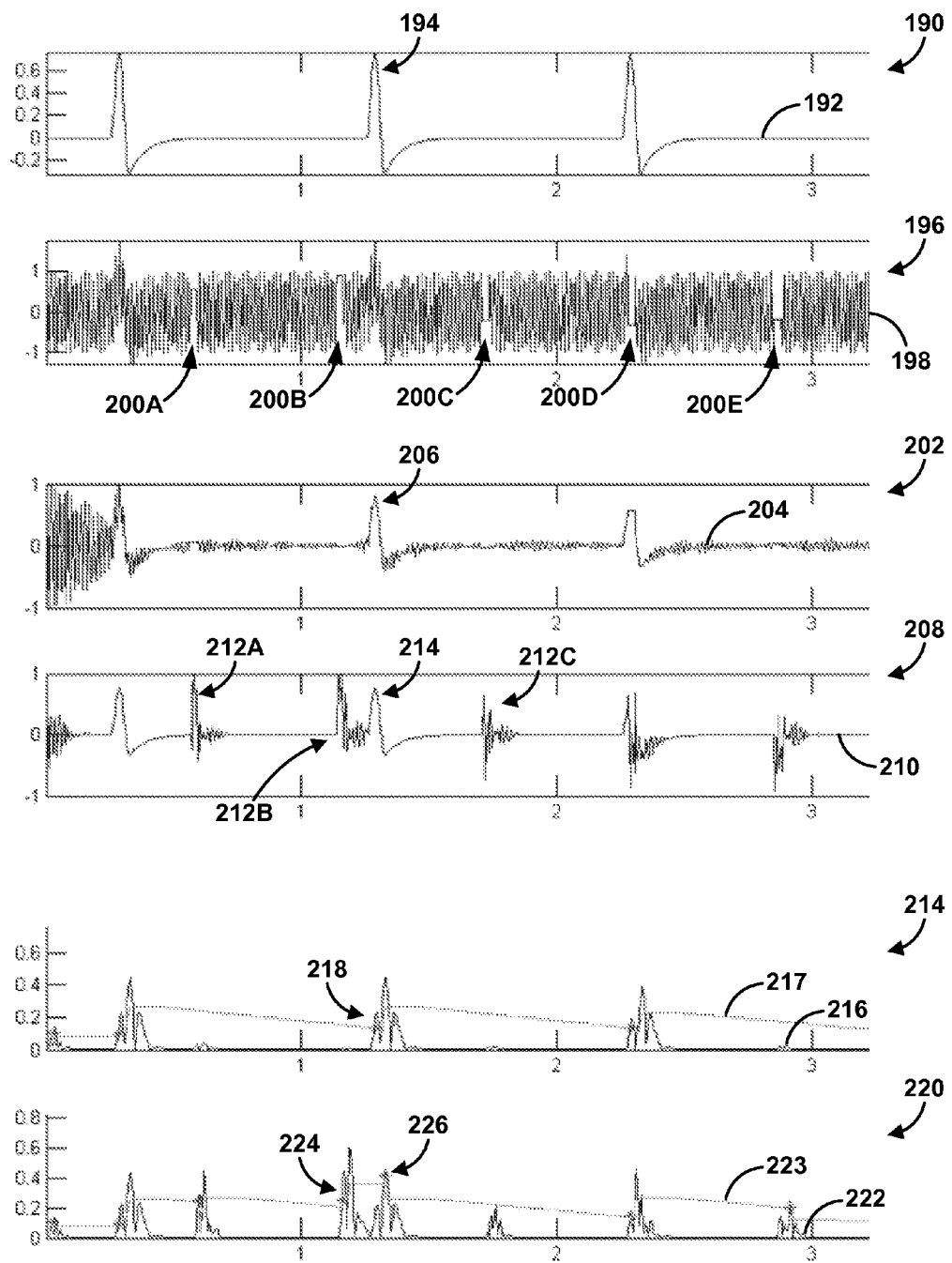
FIG. 10 illustrates graphs of an example signal indicative of normal sinus electrical activity of a heart, results of example noise filtering methods for the signal, and event detection using respective noise filtering methods.

FIG. 10 illustrates graphs of an example signal indicative of normal electrical activity of a heart, results of example noise filtering methods for the signal, and event detection using respective noise filtering methods. In the examples of each of graphs 190, 196, 202, 208, 214, and 220 show amplitude (e.g., millivolts) over time in seconds. As shown in FIG. 10, graph 190 indicates an expected cardiac activity 192 from a normal sinus rhythm of a patient. For example, expected cardiac activity 192 may include peaks 194 representative of R-waves for a patient. However, graph 196 shows that the received physiological signal 198 (e.g., a noising input signal 170 of FIG. 9) includes EMI line noise at one or more frequencies that buries the expected cardiac activity 192. Physiological signal 198 also includes blanking periods 200A, 200B, 200C, 200D, and 200E (collectively "blanking periods 200") in which no signal was received from electrodes of the medical device (e.g., IMD 16 or subcutaneous ICD 76).

Graph 208 illustrates filtered signal 210 using a typical notch filter to remove the noise at the target frequencies. Filtered signal 210 identifies peak 214 that corresponds to the expected cardiac activity 192 and peak 194 in graph 190. However, filtered signal 210 also includes peaks 212A, 212B, and 212C that result from noise and do not correspond to expected R-waves of the normal sinus rhythm in graph 190. In fact, peaks 212A, 212B, and 212C are noise artifacts resulting from blanking periods 200A, 200B, and 200C, respectively. In contrast, graph 202 illustrates filtered signal 204 by filtering physiological signal 198 according to the noise rejection model and advancement of the noise rejection model in time during blanking periods described herein. Filtered signal 204 includes peaks corresponding to the R-waves of normal sinus rhythm such as peak 206 corresponding to peak 194 of graph 190. Filtered signal 204 thus handled blanking periods 200 without any noise artifacts.

Graph 214 indicates cardiac event signal 216 generated with filtered signal 202. For example, event 218 is correctly identified as a R-wave and corresponds to peak 206 of signal 204 and peak 194 of the expected cardiac activity of a normal sinus rhythm. In this manner the noise rejection model for filtering described herein may correctly sense cardiac events even with the occurrence of blanking periods. Threshold line 217 may be used as the threshold for determining when an event (e.g., event 218) occurs within event signal 216. Threshold line 217 may change as a function of the magnitude of event signal 216 (e.g., increases in event signal 216 may increase threshold line 217 and decreases in event signal 216 may decrease threshold line 217, as shown in graph 214. In contrast, graph 220 indicates oversensing cardiac activity that can occur with typical notch filters subjected to blanking periods. Event signal 222 indicates, for example, that events 224 and 226 are R-waves and representative of a distinct cardiac cycle. However, event 224 corresponds to peak 212B which is a noise artifact caused by blanking period 200B. Therefore, an IMD (e.g., IMD 16 LPD 72, or subcutaneous ICD 76) may correctly identify heart rates shown by graph 214 with a noise rejection model instead of potential oversensing of cardiac events that can occur as shown in graph 220 by filtering noise without a noise rejection model. Threshold line 223 may be used as the threshold for determining when an event (e.g., events 224 and 226) occurs within event signal 222. Threshold line 223 may change as a function of the magnitude of event signal 222 (e.g., increases in event signal 222 may increase threshold line 223 and decreases in event signal 222 may decrease threshold line 223, as shown in graph 220.

Figure 11:
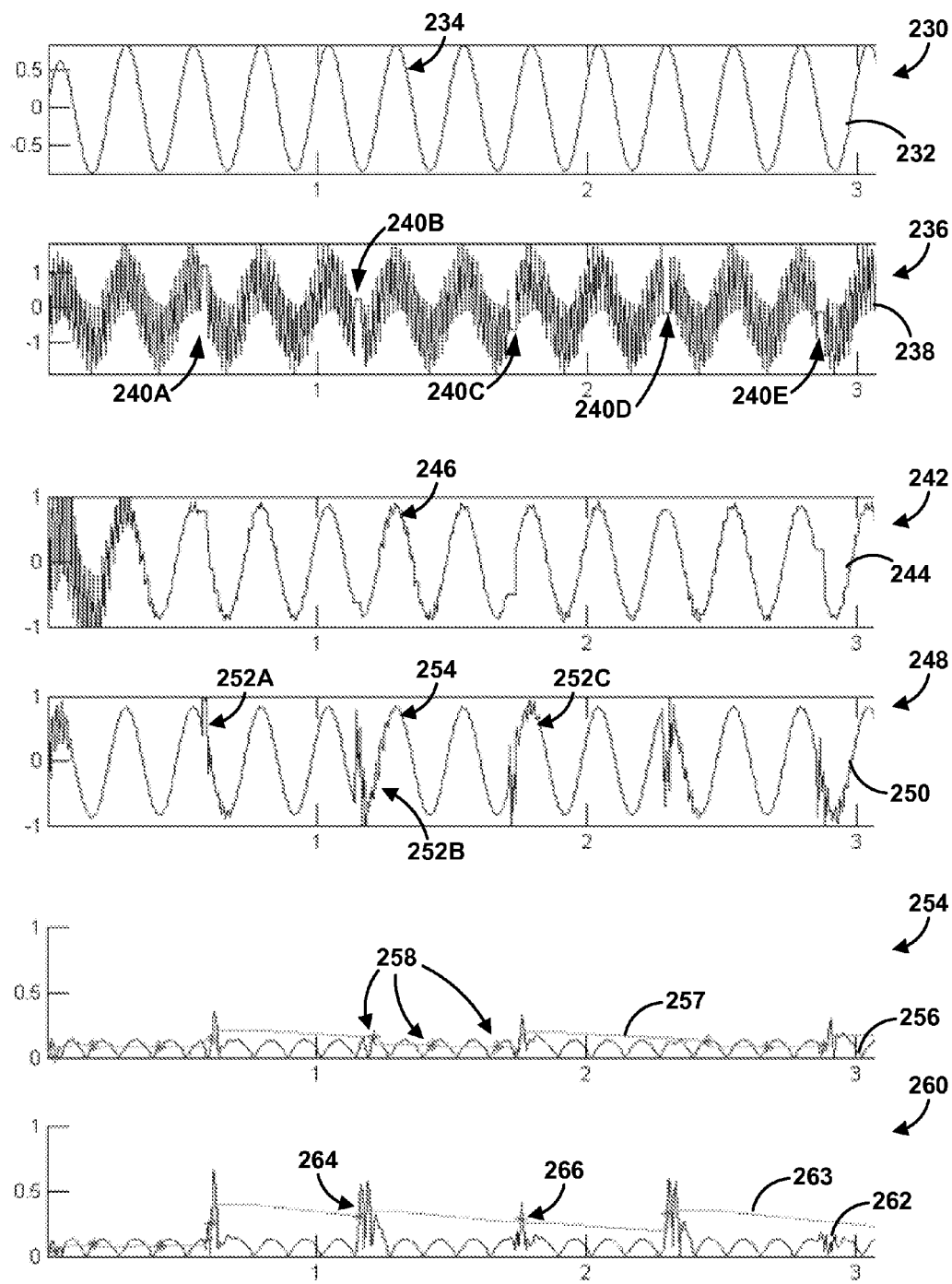
FIG. 11 illustrates graphs of an example signal indicative of ventricular fibrillation electrical activity of a heart, results of example noise filtering methods for the signal, and event detection using respective noise filtering methods.

FIG. 11 illustrates graphs of an example signal indicative of ventricular fibrillation electrical activity of a heart, results of example noise filtering methods for the signal, and event detection using respective noise filtering methods. In the examples of each of graphs 230, 236, 242, 248, 254, and 260 show amplitude (e.g., millivolts) over time in seconds. As shown in FIG. 11, graph 230 indicates an expected cardiac activity 232 from a ventricular fibrillation occurring within a patient. For example, expected cardiac activity 232 may include peaks 234 representative of R-waves, or respective cardiac cycles, for a patient. However, graph 236 shows that the received physiological signal 238 (e.g., a noising input signal 170 of FIG. 9) includes EMI line noise at one or more frequencies that buries the expected cardiac activity 232. Physiological signal 238 also includes blanking periods 240A, 240B, 240C, 240D, and 240E (collectively "blanking periods 240") in which no signal was received from electrodes of the medical device (e.g., IMD 16 or subcutaneous ICD 76).

Graph 248 illustrates filtered signal 250 using a typical notch filter to remove the noise at the target frequencies during the ventricular fibrillation and blanking periods. Filtered signal 250 identifies peak 254 that corresponds to the expected cardiac activity 232 and peak 234 in graph 230. However, filtered signal 250 also includes peaks 252A, 252B, and 252C that result from noise and do not correspond to expected R-waves of the ventricular fibrillation in graph 230. In fact, peaks 252A, 252B, and 252C are noise artifacts resulting from blanking periods 240A, 240B, and 240C, respectively. In contrast, graph 242 illustrates filtered signal 244 by filtering physiological signal 238 according to the noise rejection model and advancement of the noise rejection model in time during blanking periods described herein. Filtered signal 244 includes peaks corresponding to the R-waves of ventricular fibrillation rhythm such as peak 246 corresponding to peak 234 of graph 232. Filtered signal 244 thus handled blanking periods 240 without any noise artifacts.

Graph 254 indicates cardiac event signal 256 generated with filtered signal 244. For example, events 258 are correctly identifying cardiac cycles that that correspond to peaks 246 of filtered signal 244 and peaks 234 of the expected cardiac activity of the ventricular fibrillation in graph 230. In this manner the noise rejection model for filtering described herein may relatively accurately sense cardiac events even with the occurrence of blanking periods. Threshold line 257 may be used as the threshold for determining when an event (e.g., events 258) occurs within event signal 256. Threshold line 257 may change as a function of the magnitude of event signal 256 (e.g., increases in event signal 256 may increase threshold line 257 and decreases in event signal 256 may decrease threshold line 257, as shown in graph 254. In contrast, graph 260 indicates undersensing cardiac activity that can occur with typical notch filters subjected to blanking periods. Event signal 262 indicates, for example, that events 264 and 266 are R-waves and representative of a distinct cardiac cycle. However, events 264 and 266 do not correspond to the expected peaks 234 of the ventricular fibrillation. Indeed, event 264 corresponds to peak 252B which is noise artifact from blanking period 240B and other R-waves are not sensed due to the amplitude of the noise artifact-induced peaks being greater than the amplitude of the expected R-waves during the ventricular fibrillation. Threshold line 263 may be used as the threshold for determining when an event (e.g., events 264 and 266) occurs within event signal 262. Threshold line 263 may change as a function of the magnitude of event signal 262 (e.g., increases in event signal 262 may increase threshold line 263 and decreases in event signal 262 may decrease threshold line 263, as shown in graph 260. In other words, the increased amplitude to signal 263 due to noise artifacts may causes amplitude-dependent threshold line 263 to increase and results in undersensing cardiac cycles. Therefore, an IMD (e.g., IMD 16, LPD 72, or subcutaneous ICD 76) may correctly identify heart rates shown by graph 254 with a noise rejection model instead of potential undersensing of cardiac events that can occur as shown in graph 260 by filtering noise without a noise rejection model.

Figure 12:
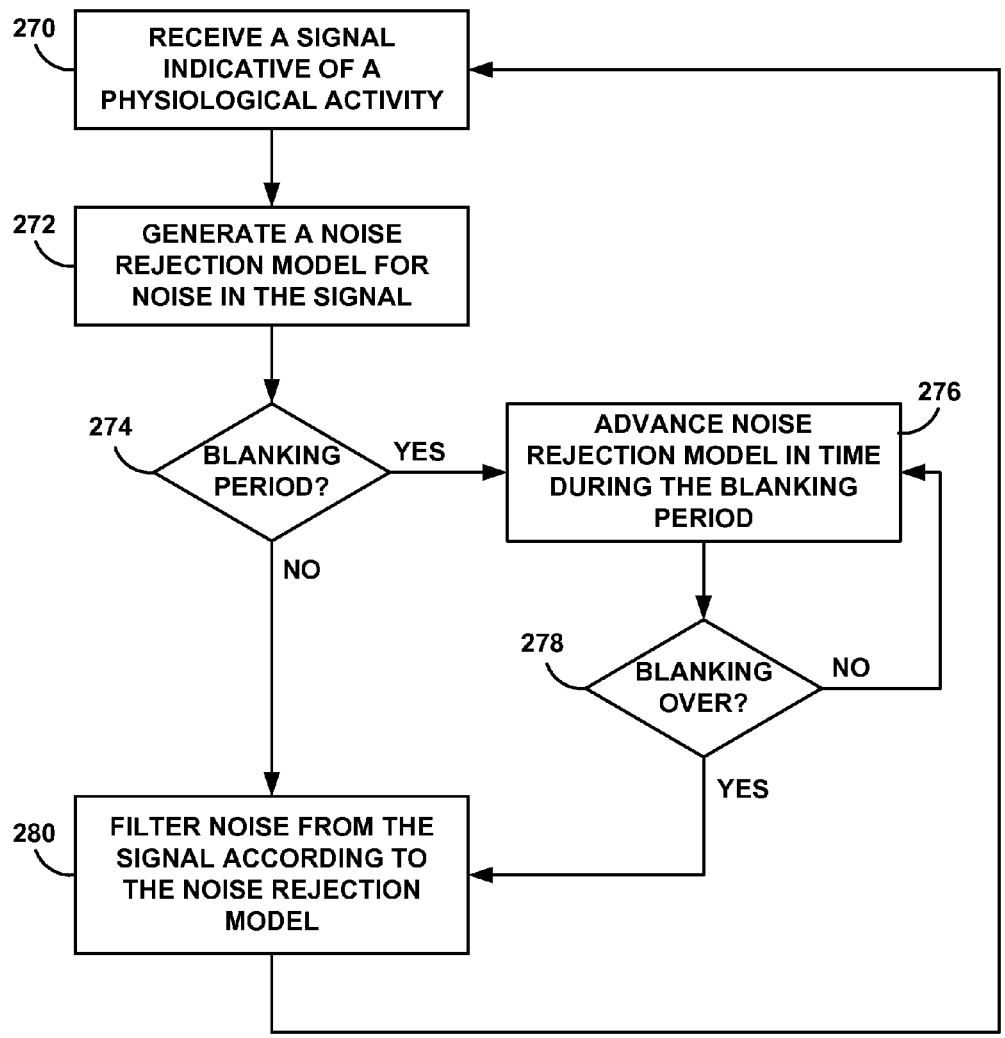
FIG. 12 is a flow diagram illustrating an example process for filtering noise from a signal according to a noise rejection model advanced in time during a blanking period.

FIG. 12 is a flow diagram illustrating an example process for filtering noise from a signal according to a noise rejection model advanced in time during a blanking period. Although described as being performed by subcutaneous ICD 76 and filtering module 145, the example method may be performed by any device, processor, module or combination of devices or processors, described herein. For example, filtering module 120 of IMD 16 and/or filtering module 136 of LPD 72 may perform the process of FIG. 12 in other examples.

As shown in FIG. 12, filtering module 145 may be configured to receive a signal (e.g., a physiological signal) indicative of a physiological activity (270). The physiological activity may be electrical activity of a heart, electrical activity of a brain, a cardiac pressure signal, or any other type of physiological activity of a patient. Filtering module 145 may then generate a noise rejection model for the noise present in the signal (272). Filtering module 145 may generate the noise rejection model in response to detecting the noise in the signal. For example, filtering module 145 may build the noise rejection model in response to noise being detected in the signal and to reject the actual noise present in the received signal. In some examples, filtering module 145 may already include a noise rejection model (e.g., a general or generic noise rejection model), but filtering module 145 may update or adapt the noise rejection model to remove the specific frequencies and/or aspects of the detected noise in the physiological signal. A pre-stored noise rejection model may be specific to one or more frequencies or may include variables that filtering module 145 adjusts to target aspects of the detected noise.

Filtering module 145 may monitor for any blanking periods (274). If filtering module 145 does not determine that a blanking period has been initiated ("NO" branch of block 274), filtering module 145 may filter noise from the signal according to the noise rejection model (280). In other words, filtering module 145 may subtract the signals of the noise rejection model from the received signal. If filtering module 145 does determine that a blanking period has been initiated ("YES" branch of block 274), filtering module 145 may advance the noise rejection model in time during the blanking period (276). Advancement of the noise rejection model may include advancing the time base of the noise rejection model to maintain a phase match between the noise rejection model and noise in the signal that will be received upon the blanking period ending. If the blanking period has not yet been terminated ("NO" branch of block 278), filtering module 145 continues to advance the noise rejection model in time (276).

If filtering module 145 determines that the blanking period has been terminated ("YES" branch of block 278), filtering module 145 may then filter the noise from the received signal according to the noise rejection model advanced in time during the blanking period (280). Filtering module 145 may then continue to receive the signal (270). In this manner, filtering the noise from the signal using the noise rejection model (e.g., subtracting the noise rejection model from the received signal) may reduce or eliminate noise artifacts in the filtered signal typically caused by resampling the noise after each blanking period terminates.

Various examples have been described. These and other examples are within the scope of the following claims. For example, although filtering of the physiological signal are directed to an electrical signal from the heart, this disclosure may also be applicable to other types of signals and blanking periods used for reasons other than a pacing pulse or defibrillation shock delivered to the patient. Furthermore, although described herein as implemented by an IMD and system including an IMD, in other examples, the techniques described herein may be implemented in an external medical device or signal processing device. An external medical device may be coupled to leads placed on the exterior surface of the patient, in some examples.

In addition, it should be noted that therapy system 10 may not be limited to treatment of a human patient. In alternative examples, therapy system 10 may be implemented in non-human patients, e.g., primates, canines, equines, pigs, and felines. These other animals may undergo clinical or research therapies that my benefit from the subject matter of this disclosure.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to IMD 16, LPD 72, subcutaneous ICD 76, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method comprising:
   receiving a signal indicative of physiological activity of a patient, wherein the signal comprises noise at one or more frequencies;
   filtering the noise from the signal according to a noise rejection model, wherein the noise rejection model predicts the noise at the one or more frequencies;
   responsive to initiation of a blanking period for the signal, advancing the noise rejection model in time during the blanking period; and
   responsive to termination of the blanking period, filtering, based on the noise rejection model advanced in time, the noise at the one or more frequencies from the signal.

2. The method of claim 1, further comprising generating, from the received signal, the noise rejection model for the one or more frequencies.

3. The method of claim 2, wherein generating the noise rejection model comprises adapting, based on the received signal, the noise rejection model over time.

4. The method of claim 2, further comprising pausing the adaption of the noise rejection model during the blanking period.

5. The method of claim 2, wherein the noise rejection model comprises a finite impulse response model, and wherein the method further comprises developing the finite impulse response model using least means square adaptation.

6. The method of claim 2, wherein generating the noise rejection model comprises detecting the noise at the one or more frequencies in the received signal and modeling the detected noise.

7. The method of claim 1, wherein advancing the noise rejection model comprises:
   calculating, for each of the one or more frequencies, a phase change of the noise rejection model for a duration of the blanking period; and
   determining, based on the phase change in the noise rejection model, an expected phase and an expected amplitude of the noise in the received signal predictive of an actual phase and an actual amplitude of the noise in the received signal at the termination of the blanking period.

8. The method of claim 1, wherein the one of more frequencies comprises one or more of 50 Hz, 60, Hz, 100 Hz, and 120 Hz.

9. The method of claim 1, wherein the blanking period comprises a blanking period during which a pacing pulse is delivered to the patient.

10. The method of claim 1, wherein the physiological activity comprises electrical activity of a heart of the patient.

11. The method of claim 10, further comprising:
    analyzing the filtered signal to detect a physiological event;
    generate an electrical stimulation therapy in response to the processor detecting the physiological event; and
    delivering the electrical stimulation therapy to the heart of the patient.

12. A device comprising:
    a filtering module configured to:
    receive a signal indicative of physiological activity of a patient, wherein the signal comprises noise at one or more frequencies;
    filter the noise from the signal according to a noise rejection model, wherein the noise rejection model predicts the noise at the one or more frequencies;

responsive to initiation of a blanking period for the signal, advance the noise rejection model in time during the blanking period; and responsive to termination of the blanking period, filter, based on the noise rejection model advanced in time, the noise at the one or more frequencies from the signal.

13. The device of claim 12, wherein the filtering module is configured to generate, from the received signal, the noise rejection model for the one or more frequencies.

14. The device of claim 13, wherein the filtering module is configured to generate the noise rejection model by adapting, based on the received signal, the noise rejection model over time.

15. The device of claim 13, wherein the noise rejection model comprises a finite impulse response model, and wherein the filtering module includes one or more processors configured to develop the finite impulse response model using least means square adaptation.

16. The device of claim 12, wherein the filtering module includes one or more processors configured to advance the noise rejection model by:

calculating, for each of the one or more frequencies, a phase change of the noise rejection model for a duration of the blanking period; and determining, based on the phase change in the noise rejection model, an expected phase and an expected amplitude of the noise in the received signal predictive of an actual phase and an actual amplitude of the noise in the received signal at the termination of the blanking period.

17. The device of claim 12, wherein the one or more frequencies comprises one or more of 50 Hz, 60, Hz, 100 Hz, and 120 Hz.

18. The device of claim 12, wherein the physiological activity comprises electrical activity of a heart of the patient.

19. The device of claim 12, wherein the device comprises an implantable medical device, and wherein the implantable medical device comprises a housing that contains the filtering module.

20. The device of claim 12, further comprising:

a processor configured to analyze the filtered signal to detect a physiological event; and a signal generator configured to generate an electrical stimulation therapy in response to the processor detecting the physiological event.

21. The device of claim 20, further comprising:

a housing configured to be implanted subcutaneously within the patient, wherein the filtering module, the processor, and the signal generator are contained within the housing;

an electrical stimulation lead coupled to the housing and including a plurality of electrodes configured to at least one of sense the signal indicative of physiological activity of the patient or deliver the electrical stimulation therapy to the patient.

22. The device of claim 21, wherein the electrodes of the electrical stimulation lead sense the signal indicative of the physiological activity from an extravascular location.

23. The device of claim 22, wherein the extravascular location is one of a subcutaneous location and a substernal location.

24. The device of claim 20, further comprising:

a housing sized to be implanted within a chamber of the heart and having at least two electrodes on the housing, wherein the filtering module, the processor, and the signal generator are contained within the housing; and wherein the at least two electrodes on the housing sense the signal indicative of the physiological activity.

25. A system comprising:

means for receiving a signal indicative of physiological activity of a patient, wherein the signal comprises noise at one or more frequencies;

means for filtering the noise from the signal according to a noise rejection model, wherein the noise rejection model predicts the noise at the one or more frequencies;

means for, responsive to initiation of a blanking period for the signal, advancing the noise rejection model in time during the blanking period; and means for, responsive to termination of the blanking period, filtering, based on the noise rejection model advanced in time, the noise at the one or more frequencies from the signal.

* * * * *